United States Patent
Goldman et al.

(10) Patent No.: US 11,035,865 B2
(45) Date of Patent: Jun. 15, 2021

(54) SEROLOGIC ASSAY OF LIVER FIBROSIS

(71) Applicant: Georgetown University, Washington, DC (US)

(72) Inventors: Radoslav Goldman, Reston, VA (US); Miloslav Sanda, Arlington, VA (US)

(73) Assignee: GEORGETOWN UNIVERSITY, Washington, DC (US)

( * ) Notice: Subject to any disclaimer, the term of this patent is extended or adjusted under 35 U.S.C. 154(b) by 275 days.

(21) Appl. No.: 16/329,926

(22) PCT Filed: Aug. 31, 2017

(86) PCT No.: PCT/US2017/049563
§ 371 (c)(1),
(2) Date: Mar. 1, 2019

(87) PCT Pub. No.: WO2018/045145
PCT Pub. Date: Mar. 8, 2018

(65) Prior Publication Data
US 2019/0242907 A1  Aug. 8, 2019

Related U.S. Application Data

(60) Provisional application No. 62/383,020, filed on Sep. 2, 2016.

(51) Int. Cl.
*G01N 33/68* (2006.01)
*C07K 14/47* (2006.01)

(52) U.S. Cl.
CPC ......... *G01N 33/6893* (2013.01); *C07K 14/47* (2013.01); *G01N 33/6827* (2013.01);
(Continued)

(58) Field of Classification Search
None
See application file for complete search history.

(56) References Cited

U.S. PATENT DOCUMENTS

2007/0037221 A1    2/2007   Block et al.
2012/0190576 A1    7/2012   Narimatsu et al.
(Continued)

OTHER PUBLICATIONS

Sanda et al. (2013) "LC-MS3 Quantification of O-Glycopeptides in Human Serum," Electrophoresis. 34(16):2342-2349.
(Continued)

*Primary Examiner* — Xiaoyun R Xu
(74) *Attorney, Agent, or Firm* — Lathrop GPM LLP; Alan W. Steele

(57) ABSTRACT

Provided are in vitro serologic methods of assessing the presence of, and assessing the progression of, liver fibrosis in a subject. Also provided are methods of assessing efficacy of an agent for the treatment of liver fibrosis, and methods of treating liver fibrosis. The methods involve quantitatively measuring di-sialylated and mono-sialylated O-glycoforms of a peptide fragment of hemopexin (HPX) in a test serum sample obtained from a test subject, and comparing the measured amounts of di-sialylated and mono-sialylated O-glycoforms of the peptide fragment of hemopexin to a reference amount. In certain embodiments, the measuring is performed using LC-MS/MS-MRM (liquid chromatography/tandem mass spectrometry/multiple reaction monitoring). In certain embodiments, the measuring is performed using LC/MS3 (liquid chromatography with triple-stage mass spectrometric detection).

20 Claims, 7 Drawing Sheets
Specification includes a Sequence Listing.

(52) U.S. Cl.
    CPC ... *G01N 33/6848* (2013.01); *G01N 2800/085* (2013.01); *G01N 2800/52* (2013.01)

(56) References Cited

U.S. PATENT DOCUMENTS

| | | |
|---|---|---|
| 2014/0235494 A1 | 8/2014 | Schmidt et al. |
| 2015/0323551 A1 | 11/2015 | Jacobs et al. |
| 2016/0090583 A1 | 3/2016 | Super et al. |

OTHER PUBLICATIONS

Comunale et al., "Linkage Specific Fucosylation of Alpha-1-Antitrypsin in Liver Cirrhosis and Cancer Patients: Implications for a Biomarker of Hepatocellular Carcinoma", PLoS ONE, vol. 5, Issue 1, e12419 2010.

Debruyne et al., "Diagnostic Value of the Hemopexin N-Glycan profile in Hepatocellular Carcinoma Patients", Clinical Chem., vol. 56, Issue 5, pp. 823-831, 2010.

Di Bisceglie et al., "Prolonged Therapy of Advanced Chronic Hepatitis C with Low-Dose Peginterferon", New England Journal of Medicine 359;23 pp. 2429-2441, Dec. 4, 2008.

Lok et al., "Evolution of Hepatic Steatosis in Patients with Advanced Hepatitis C: Results from the Hepatitis C Antiviral Long-Term Treatment Against Cirrhosis (HALT-C) Trial", Hepatology vol. 49, No. 6, pp. 1828-1837, Jun. 2009.

Mehta et al., "Increased Levels of Galactose-Deficient Anti-Gal Immunoglobulin G in the Sera of Hepatitis C Virus-Infected Individuals with Fibrosis and Cirrhosis", Journal of Virology, vol. 82, No. 3, pp. 1259-1270, Feb. 2008.

Vanderschaeghe et al., "GlycoFibroTest Is a Highly Performant Liver Fibrosis Biomarker Derived from DNA Sequencer-based Serum Protein Glycomics", Molecular Cell Proteomics 8.5, pp. 986-994, Jan. 2009.

SEROLOGIC ASSAY OF LIVER FIBROSIS

RELATED APPLICATIONS

This application is the 371 national stage of International Patent Application No. PCT/US2017/049563, filed on Aug. 31, 2017, which claims benefit of priority to U.S. Provisional Patent Application No. 62/383,020, filed on Sep. 2, 2016, the entire contents of which are incorporated herein by reference.

STATEMENT REGARDING FEDERALLY SPONSORED RESEARCH OR DEVELOPMENT

This invention was made with government support under grant numbers UO1 CA168926 and RO1 CA135069 awarded by the National Institutes of Health, and grant number P30 CA51008 awarded by the National Cancer Institute. The government has certain rights in the invention.

SEQUENCE LISTING

The instant application contains a Sequence Listing which has been submitted electronically in ASCII format and is hereby incorporated by reference in its entirety. Said ASCII copy, created on Aug. 29, 2017, is named GUS-019PC_ST25.txt and is 567 bytes in size.

BACKGROUND

Fibrosis, or the net accumulation of extracellular matrix (ECM) or scar, has long been recognized in patients with chronic liver disease, yet until recently it was considered intractable. Since Perez-Tamayo, *Pathol Annu* 1979; 14 (Pt 2): 183-213 (1979) presciently predicted the reversibility of fibrosis following the characterization of collagenase activity in liver that could degrade ECM molecules, intense research effort ultimately has led to the identification of a number of cells, mediators, and intracellular signals that culminate in hepatic scar. This, in turn, has led to rational mechanism-based antifibrotic strategies that are now being tested in clinical trials. Very recently, particularly since the advent of direct-acting antiviral therapies, it has been demonstrated that liver fibrosis is reversible and cirrhosis may regress in some cases. The regression of cirrhosis has been observed in patients with iron and copper overload, alcohol-induced liver injury, chronic hepatitis B, C and D, hemochromatosis, secondary biliary cirrhosis, non-alcoholic steatohepatitis (NASH) and autoimmune hepatitis. Among these diseases, reversibility seems especially likely in patients in whom hepatitis B (HBV) therapy suppresses viral replication, however, cirrhosis reversion is now also reported in hepatitis C (HCV) patients following sustained virologic response. Overall, up to 70% of patients with HBV or HCV cirrhosis will demonstrate reversibility on follow-up biopsies, but more extensive data for HCV are anticipated now that sustained virologic response rates exceed 90% using direct-acting antiviral therapies. Moreover, when reversal occurs in HCV, it leads to improved clinical outcomes, reduced portal pressure and decreased all-cause mortality.

Hepatitis C virus is a leading cause of chronic liver disease in the United States. Approximately 20% of chronic HCV cases develop liver cirrhosis and 2.5% develop hepatocellular carcinoma (HCC) which appears most commonly in cirrhotic livers. While the recently available HCV treatment regimens are expected eventually to decrease the burden of liver disease, the large number of unidentified and untreated HCV infections, uncertain reversibility of liver damage, and increasing impact of nonalcoholic fatty liver disease (NAFLD)/nonalcoholic steatohepatitis (NASH) suggest that non-invasive monitoring of liver disease remains an important clinical tool.

Biopsy is the diagnostic standard for monitoring of liver disease in spite of its invasive nature, associated complications, and inconsistent sampling. It is expected that non-invasive detection of liver fibrosis at a potentially reversible stage, improved predictive models of liver disease progression, and detection of resectable early stage HCC will have major impacts on disease outcomes. This has stimulated considerable interest in non-invasive serologic, liver function, and imaging tests that could complement biopsy in liver disease classification. Despite these efforts, alternatives to biopsy have not yet reached general acceptance, and the search for viable options continues.

Glycosylation is a common and diverse modification of proteins secreted by the liver. Two major pathways of glycosylation of secretory proteins have been described: N-glycosylation of asparagine (Asn) in the sequence Asn-X-Ser/Thr (X≠Pro); and mucin-type O-glycosylation of serine or threonine (Ser/Thr) without a well-defined sequence motif. Diversity and functions of the proteome are substantially expanded by these modifications. It has been reported that changes in certain types of protein glycosylation accompany the development of fibrosis, cirrhosis, and HCC. Unusual N-glycoforms of immunoglobulins as well as liver-secreted proteins have been proposed as the basis for serologic tests for monitoring liver disease. Vanderschaeghe et al., *Mol Cell Proteomics* 8: 986-994 (2009); Mehta et al., *J Virol* 82: 1259-1270 (2008); Debruyne et al., *Physiol Rev* 56: 823-831 (2010). Methodological improvements have been reported to show that O-glycosylation of proteins is as common and important as N-glycosylation; however, until now O-glycosylation of liver-secreted proteins has been unused in serologic assays of liver disease.

Hemopexin (HPX) is a 439 amino acid protein (GenBank Accession No. NP_000604) secreted mainly by hepatocytes. It forms a complex with free heme in the bloodstream, and the complex is cleared from circulation by a hepatocyte-specific membrane receptor. It was reported that serum concentration of HPX (0.4-1.5 g/L) does not vary significantly in liver disease. Varki et al., *Essentials of Glycobiology*, 2nd edn., Cold Spring Harbor, N.Y.: Cold Spring Harbor Laboratory Press; 2009. While N-glycosylation of HPX is reported to be altered in liver disease, until now O-glycosylation of HPX has not been examined in this context.

A need still exists for validated non-invasive markers of liver fibrosis progression and regression that can supplant biopsy and shorten the duration of clinical trials.

SUMMARY OF THE INVENTION

An aspect of the invention is an in vitro method of assessing liver fibrosis in a subject, comprising quantitatively measuring di-sialylated and mono-sialylated O-glycoforms of a peptide fragment of hemopexin in a test serum sample obtained from a test subject, wherein the amino acid sequence of the peptide fragment of hemopexin comprises TPLPPTSAHGNVAEGETKPDPVTER (SEQ ID NO:1);

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from a reference subject, wherein the reference subject is free of liver fibrosis; and identifying the test subject as having liver fibrosis when the measured amount of di-sialylated O-glycoform of the peptide fragment of hemopexin in the test serum sample is increased, and the measured amount of mono-sialylated O-glycoform of the peptide fragment of hemopexin in the test serum sample is decreased, as compared to corresponding measured amounts in the reference serum sample.

An aspect of the invention is an in vitro method of assessing liver fibrosis in a subject, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the subject, wherein the reference serum sample was obtained from the subject earlier in time than the test serum sample; and identifying the subject as having increased liver fibrosis when the measured amount of di-sialylated O-glycoform of the peptide fragment of hemopexin in the test serum sample is increased, and the measured amount of mono-sialylated O-glycoform of the peptide fragment of hemopexin in the test serum sample is decreased, as compared to corresponding measured amounts in the reference serum sample, or identifying the subject as having decreased liver fibrosis when the measured amount of di-sialylated O-glycoform of the peptide fragment of hemopexin in the test serum sample is decreased, and the measured amount of mono-sialylated O-glycoform of the peptide fragment of hemopexin in the test serum sample is increased, as compared to corresponding measured amounts in the reference serum sample.

An aspect of the invention is a method of assessing efficacy of an agent for the treatment of liver fibrosis, wherein the agent is selected from the group consisting of anti-fibrosis agents and candidate anti-fibrosis agents, comprising quantitatively measuring di-sialylated and mono-sialylated O-glycoforms of a peptide fragment of hemopexin in a first test serum sample obtained from a subject, wherein the amino acid sequence of the peptide fragment of hemopexin comprises SEQ ID NO:1;

administering the agent to the subject;

quantitatively measuring di-sialylated and mono-sialylated O-glycoforms of the peptide fragment of hemopexin in a second test serum sample obtained from the subject;

comparing the measured amounts of di-sialylated and mono-sialylated O-glycoforms of the peptide fragment of hemopexin in the first test serum sample to the measured amounts of di-sialylated and mono-sialylated O-glycoforms of the peptide fragment of hemopexin in the second serum sample, wherein the second test serum sample was obtained after the administering and later in time than the first test serum sample; and identifying the agent as effective for treating liver fibrosis when the measured amount of di-sialylated O-glycoform of the peptide fragment of hemopexin in the second test serum sample is decreased, and the measured amount of mono-sialylated O-glycoform of the peptide fragment of hemopexin in the second test serum sample is increased, as compared to corresponding measured amounts in the first test serum sample.

In certain embodiments, the method further comprises identifying the agent as ineffective for treating liver fibrosis when the measured amount of di-sialylated O-glycoform of the peptide fragment of hemopexin in the second test serum sample is increased, and the measured amount of mono-sialylated O-glycoform of the peptide fragment of hemopexin in the second test serum sample is decreased, as compared to corresponding measured amounts in the first test serum sample.

An aspect of the invention is a method of treating liver fibrosis, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the subject, wherein the reference serum sample was obtained earlier in time than the test serum sample;

identifying the subject as having increased liver fibrosis when the measured amount of di-sialylated O-glycoform of the peptide fragment of hemopexin in the test serum sample is increased, and the measured amount of mono-sialylated O-glycoform of the peptide fragment of hemopexin in the test serum sample is decreased, as compared to corresponding measured amounts in the reference serum sample; and administering to the subject having increased liver fibrosis an initial amount or an increased amount of an anti-fibrosis agent.

An aspect of the invention is a method of treating liver fibrosis, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises TPLPPTSAHGNVAEGETKPDPVTER (SEQ ID NO:1);

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the test subject, wherein the reference serum sample was obtained earlier in time than the test serum sample;

identifying the test subject as having decreased liver fibrosis when the measured amount of di-sialylated O-glycoform of the peptide fragment of hemopexin in the test serum sample is decreased, and the measured amount of mono-sialylated O-glycoform of the peptide fragment of hemopexin in the test serum sample is increased, as compared to corresponding measured amounts in the reference serum sample; and administering to the subject having decreased liver fibrosis a continued amount or a decreased amount of an anti-fibrosis agent.

In accordance with each of the foregoing aspects and embodiments, in certain embodiments, the amino acid sequence of the peptide fragment of hemopexin consists of SEQ ID NO:1.

In accordance with each of the foregoing aspects and embodiments, in certain embodiments, the amino acid sequence of the peptide fragment of hemopexin consists of SEQ ID NO:1.

In accordance with each of the foregoing aspects and embodiments, in certain embodiments, the measuring comprises LC-MS/MS-MRM (liquid chromatography/tandem mass spectrometry/multiple reaction monitoring).

In accordance with each of the foregoing aspects and embodiments, in certain embodiments, the measuring comprises LC/MS3 (liquid chromatography with triple-stage mass spectrometric detection).

In accordance with the foregoing aspects and embodiments, in certain embodiments, agent is selected from the group consisting of interferon alfa-2b, PEG-interferon alfa-2b, PEG-interferon alfa-2a, lamivudine (Epivir), adefovir (Hepsera), telbivudine (Tyzeka), entecavir (Baraclude), ribavirin, boceprivir (Victrelis), telaprevir (Incivek), simeprevir (Olysio), sofosbuvir (Sovaldi), ledipasvir/sofosbuvir (Harvoni), sofosbuvir/velpatasvir, ombitasvir/paritaprevir/ritonavir (Technivie), daclatasvir (Daklinza), dasabuvir, CB1 antagonist (e.g., rimonabant), 5HT-2B receptor antagonist, angiotensin-converting enzyme (ACE) inhibitor, angiotensin II type 1 (AT1) receptor blocker endothelin 1 (ET-1) receptor antagonist, adiponectin, ghrelin, PDGF receptor antagonist, imatinib, nilotinib, tissue inhibitors of metalloproteinases (TIMPs), sulfasalazine, gliotoxin, nonsteroidal anti-inflammatory drugs (NSAIDs), and any combination thereof.

DETAILED DESCRIPTION

Figure 2:
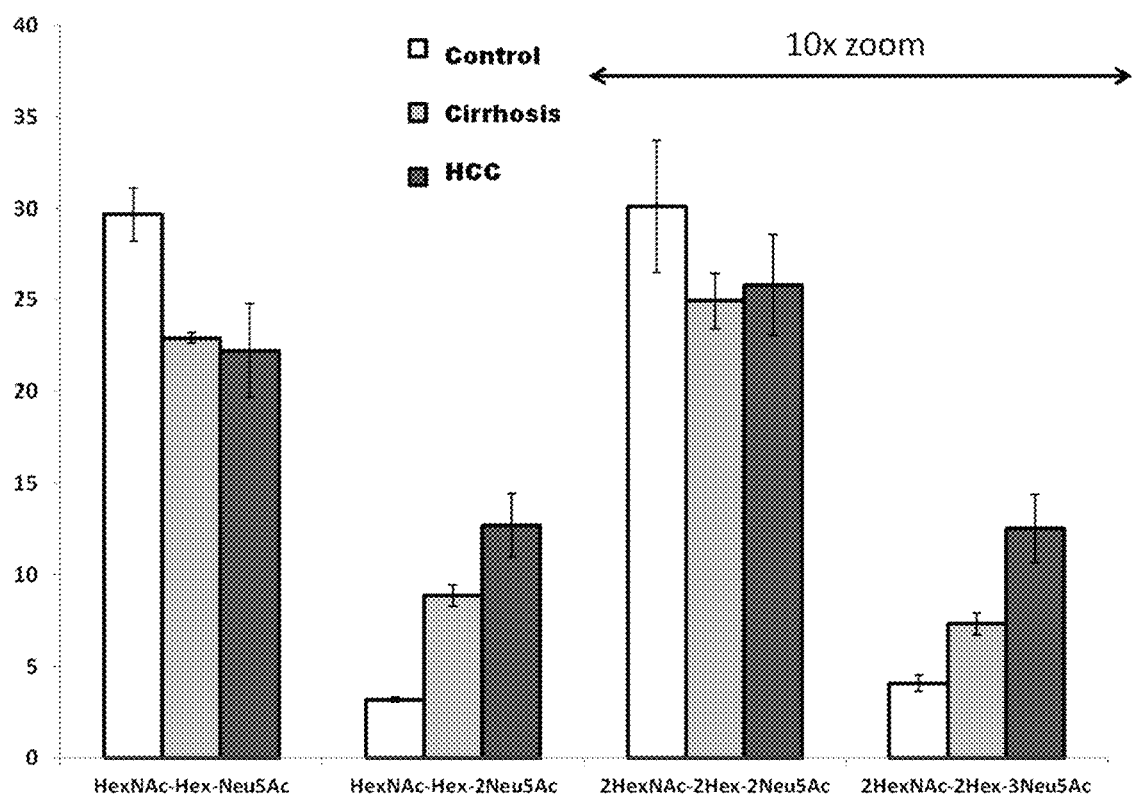
FIG. 2 is a bar graph depicting quantification of mono-(HexNAc-Hex-Neu5Ac and 2HexNAc-2Hex-2Neu5Ac) and bi-(HexNAc-Hex-2Neu5Ac and 2HexNAc-2Hex-3Neu5Ac) sialylated O-glycopeptides of hemopexin. Shown are results from pooled plasma of healthy volunteers (white bars), cirrhotic subjects (grey bars), and HCC subjects (black bars). Intensities of the peptides, doubly O-glycosylated at T1 and T6 (right side of the figure), are 10-times magnified. Results represent extracted ion chromatogram of precursor ions normalized to an internal peptide of HPX and error bars represent analysis of two different plasma pools (samples of 5 participants in each pool) as described in the Examples.
Figure 6:
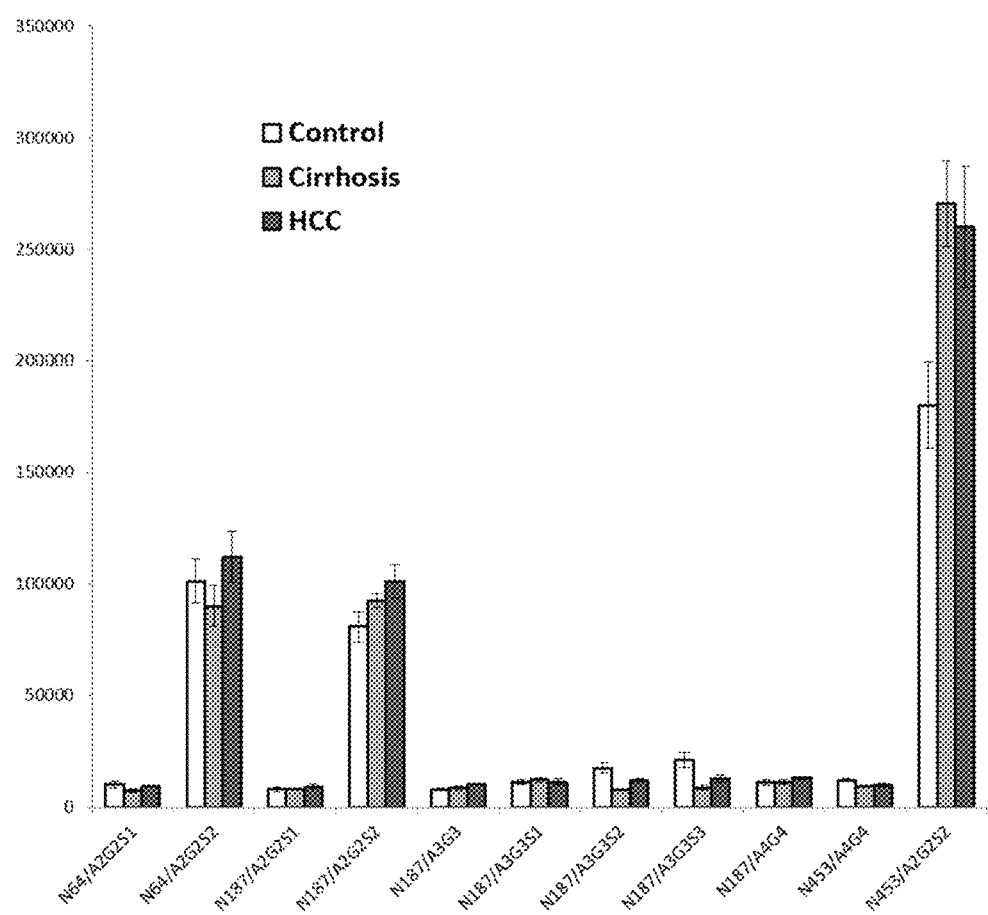
FIG. 6 is a graph depicting quantification of detected N-glycopeptides at three different N-glycosylation sequons (N64, N187 and N453) of HPX isolated from pooled plasma of healthy volunteers (white bars), cirrhotic patients (grey bars), and HCC patients (black bars). Results represent XIC of precursor ions normalized to an internal peptide of HPX, and error bars represent parallel analysis of two different plasma pools (samples of 5 participants in each pool) as described in the Examples. AxGySz denotes the following: number of antennas (A), galactoses (G), and sialic acids (S) associated with each sequon.

The present invention is based in part on the discovery by the inventors of certain site-specific O-glycoforms of HPX in liver disease (Table 5). As disclosed herein, fifteen O-glycoforms were detected, of which two major glycoforms, HexNAc-Gal-Neu5Ac and HexNAc-Gal-2Neu5Ac, represent approximately 85% of the total. Additional minor O-glycoforms represent multiplication of the same structures attached to additional serine/threonine residues of the same tryptic peptide. In contrast to the increased occupancy of the additional O-glycosites of HPX observed in congenital disorders of glycosylation, changes in occupancy of additional sites in liver disease were not observed, but rather increased sialylation of the O-glycan attached to the N-terminal threonine (T1) of HPX. Of note, the increase in sialylation is specific to the O-glycans of HPX. N-glycopeptides in the tryptic digests of HPX were observed simultaneously and do not increase in their sialylation except for an approximately 30% increase in case of one of the N-glycopeptides (FIG. 6). This is marginal compared to the several-fold increase in the di-sialylated O-glycoform of HPX observed in the same samples (FIG. 2).

The invention relates in part to targeted LC-MS3 and LC-MS/MS-MRM assays for quantification of the di-sialylated and mono-sialylated glycoforms. The assays, adapted to the analysis on the 6500 QTRAP mass spectrometer, can be used to determine the ratio, here referred to as "S-HPX", between di-sialylated and mono-sialylated O-glycoforms of HPX. Analysis of results using the two targeted methods shows that quantification of S-HPX by LC-MS/MS-MRM directly in serum has lower variability (RSD=6% in repeated analysis of a QC sample) compared to the LC-MS3 assays (RSD=18%) and has sufficient sensitivity on the 6500 QTRAP instrument to achieve quantification in all samples examined.

Also as disclosed herein, S-HPX increases progressively in fibrotic and cirrhotic participants compared to disease-free controls (FIG. 3). The LC-MS/MS-MRM assay has adequate analytical performance for direct quantification of S-HPX in serum samples which could facilitate its development into a reliable clinical test. The combined novelty of monitoring specific O-glycoforms of HPX by the newly optimized LC-MS/MS-MRM workflow makes quantification of S-HPX in liver disease unique and efficient.

An aspect of the invention is an in vitro method of assessing liver fibrosis in a subject, comprising
quantitatively measuring di-sialylated and mono-sialylated O-glycoforms of a peptide fragment of hemopexin in a test serum sample obtained from a test subject, wherein the amino acid sequence of the peptide fragment of hemopexin comprises the N-terminal 25 amino acid residues of hemopexin, TPLPPTSAHGNVAEGETKPDPVTER (SEQ ID NO:1);
comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from a reference subject, wherein the reference subject is free of liver fibrosis; and
identifying the test subject as having liver fibrosis when the measured amount of di-sialylated O-glycoform of the peptide fragment of hemopexin in the test serum sample is increased as compared to corresponding measured amounts in the reference serum sample.

An aspect of the invention is an in vitro method of assessing liver fibrosis in a subject, comprising
quantitatively measuring di-sialylated and mono-sialylated O-glycoforms of a peptide fragment of hemopexin in a test serum sample obtained from a test subject, wherein the amino acid sequence of the peptide fragment of hemopexin comprises the N-terminal 25 amino acid residues of hemopexin, TPLPPTSAHGNVAEGETKPDPVTER (SEQ ID NO:1);
comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from a reference subject, wherein the reference subject is free of liver fibrosis; and
identifying the test subject as having liver fibrosis when the measured amount of mono-sialylated O-glycoform of the peptide fragment of hemopexin in the test serum sample is decreased as compared to corresponding measured amounts in the reference serum sample.

An aspect of the invention is an in vitro method of assessing liver fibrosis in a subject, comprising
quantitatively measuring di-sialylated and mono-sialylated O-glycoforms of a peptide fragment of hemopexin in a test serum sample obtained from a test subject, wherein the amino acid sequence of the peptide fragment of hemopexin comprises the N-terminal 25 amino acid residues of hemopexin, TPLPPTSAHGNVAEGETKPDPVTER (SEQ ID NO:1);
comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from a reference subject, wherein the reference subject is free of liver fibrosis; and
identifying the test subject as having liver fibrosis when the measured amount of di-sialylated O-glycoform of the peptide fragment of hemopexin in the test serum sample is increased, and the measured amount of mono-sialylated O-glycoform of the peptide fragment of hemopexin in the test serum sample is decreased, as compared to corresponding measured amounts in the reference serum sample.

In certain embodiments, the amino acid sequence of the peptide fragment of hemopexin consists of SEQ ID NO:1.

In certain embodiments, the measuring comprises LC-MS/MS-MRM (liquid chromatography/tandem mass spectrometry/multiple reaction monitoring), as described herein.

In certain embodiments, the measuring comprises LC/MS3 (liquid chromatography with triple-stage mass spectrometric detection), as described herein.

An aspect of the invention is an in vitro method of assessing liver fibrosis in a subject, comprising
quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;
comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the subject, wherein the reference serum sample was obtained from the subject earlier in time than the test serum sample; and
identifying the subject as having increased liver fibrosis when the measured amount of di-sialylated O-glycoform of the peptide fragment of hemopexin in the test serum sample is increased as compared to corresponding measured amounts in the reference serum sample.

An aspect of the invention is an in vitro method of assessing liver fibrosis in a subject, comprising
quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;
comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the subject, wherein the reference serum sample was obtained from the subject earlier in time than the test serum sample; and
identifying the subject as having decreased liver fibrosis when the measured amount of mono-sialylated O-glycoform of the peptide fragment of hemopexin in the test serum sample is increased as compared to corresponding measured amounts in the reference serum sample.

An aspect of the invention is an in vitro method of assessing liver fibrosis in a subject, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the subject, wherein the reference serum sample was obtained from the subject earlier in time than the test serum sample; and identifying the subject as having increased liver fibrosis when the measured amount of di-sialylated O-glycoform of the peptide fragment of hemopexin in the test serum sample is increased, and the measured amount of mono-sialylated O-glycoform of the peptide fragment of hemopexin in the test serum sample is decreased, as compared to corresponding measured amounts in the reference serum sample, or identifying the subject as having decreased liver fibrosis when the measured amount of di-sialylated O-glycoform of the peptide fragment of hemopexin in the test serum sample is decreased, and the measured amount of mono-sialylated O-glycoform of the peptide fragment of hemopexin in the test serum sample is increased, as compared to corresponding measured amounts in the reference serum sample.

In certain embodiments, the amino acid sequence of the peptide fragment of hemopexin consists of SEQ ID NO:1.

In certain embodiments, the measuring comprises LC-MS/MS-MRM (liquid chromatography/tandem mass spectrometry/multiple reaction monitoring), as described herein.

In certain embodiments, the measuring comprises LC/MS3 (liquid chromatography with triple-stage mass spectrometric detection), as described herein.

An aspect of the invention is a method of assessing efficacy of an agent for the treatment of liver fibrosis, wherein the agent is selected from the group consisting of anti-fibrosis agents and candidate anti-fibrosis agents, comprising quantitatively measuring di-sialylated and mono-sialylated O-glycoforms of a peptide fragment of hemopexin in a first test serum sample obtained from a subject, wherein the amino acid sequence of the peptide fragment of hemopexin comprises SEQ ID NO:1;

administering the agent to the subject;

quantitatively measuring di-sialylated and mono-sialylated O-glycoforms of the peptide fragment of hemopexin in a second test serum sample obtained from the subject;

comparing the measured amounts of di-sialylated and mono-sialylated O-glycoforms of the peptide fragment of hemopexin in the first test serum sample to the measured amounts of di-sialylated and mono-sialylated O-glycoforms of the peptide fragment of hemopexin in the second serum sample, wherein the second test serum sample was obtained after the administering and later in time than the first test serum sample; and identifying the agent as effective for treating liver fibrosis when the measured amount of di-sialylated O-glycoform of the peptide fragment of hemopexin in the second test serum sample is decreased as compared to corresponding measured amounts in the first test serum sample.

An aspect of the invention is a method of assessing efficacy of an agent for the treatment of liver fibrosis, wherein the agent is selected from the group consisting of anti-fibrosis agents and candidate anti-fibrosis agents, comprising quantitatively measuring di-sialylated and mono-sialylated O-glycoforms of a peptide fragment of hemopexin in a first test serum sample obtained from a subject, wherein the amino acid sequence of the peptide fragment of hemopexin comprises SEQ ID NO:1;

administering the agent to the subject;

quantitatively measuring di-sialylated and mono-sialylated O-glycoforms of the peptide fragment of hemopexin in a second test serum sample obtained from the subject;

comparing the measured amounts of di-sialylated and mono-sialylated O-glycoforms of the peptide fragment of hemopexin in the first test serum sample to the measured amounts of di-sialylated and mono-sialylated O-glycoforms of the peptide fragment of hemopexin in the second serum sample, wherein the second test serum sample was obtained after the administering and later in time than the first test serum sample; and identifying the agent as effective for treating liver fibrosis when the measured amount of mono-sialylated O-glycoform of the peptide fragment of hemopexin in the second test serum sample is increased as compared to corresponding measured amounts in the first test serum sample.

An aspect of the invention is a method of assessing efficacy of an agent for the treatment of liver fibrosis, wherein the agent is selected from the group consisting of anti-fibrosis agents and candidate anti-fibrosis agents, comprising quantitatively measuring di-sialylated and mono-sialylated O-glycoforms of a peptide fragment of hemopexin in a first test serum sample obtained from a subject, wherein the amino acid sequence of the peptide fragment of hemopexin comprises SEQ ID NO:1;

administering the agent to the subject;

quantitatively measuring di-sialylated and mono-sialylated O-glycoforms of the peptide fragment of hemopexin in a second test serum sample obtained from the subject;

comparing the measured amounts of di-sialylated and mono-sialylated O-glycoforms of the peptide fragment of hemopexin in the first test serum sample to the measured amounts of di-sialylated and mono-sialylated O-glycoforms of the peptide fragment of hemopexin in the second serum sample, wherein the second test serum sample was obtained after the administering and later in time than the first test serum sample; and identifying the agent as effective for treating liver fibrosis when the measured amount of di-sialylated O-glycoform of the peptide fragment of hemopexin in the second test serum sample is decreased, and the measured amount of mono-sialylated O-glycoform of the peptide fragment of hemopexin in the second test serum sample is increased, as compared to corresponding measured amounts in the first test serum sample.

In certain embodiments, the amino acid sequence of the peptide fragment of hemopexin consists of SEQ ID NO:1.

In certain embodiments, the measuring comprises LC-MS/MS-MRM (liquid chromatography/tandem mass spectrometry/multiple reaction monitoring), as described herein.

In certain embodiments, the measuring comprises LC/MS3 (liquid chromatography with triple-stage mass spectrometric detection), as described herein.

In certain embodiments, the method further comprises identifying the agent as ineffective for treating liver fibrosis when the measured amount of di-sialylated O-glycoform of the peptide fragment of hemopexin in the second test serum sample is increased, and the measured amount of mono-sialylated O-glycoform of the peptide fragment of hemopexin in the second test serum sample is decreased, as compared to corresponding measured amounts in the first test serum sample.

In certain embodiments, the agent is an anti-fibrosis agent. As used herein, an "anti-fibrosis agent" is an agent that inhibits fibrosis in a subject. As used herein, an "anti-fibrosis agent" is an agent that inhibits fibrosis in a human subject. In an embodiment, the anti-fibrosis agent is an agent that inhibits liver fibrosis in a subject. In an embodiment, the anti-fibrosis agent is an agent that inhibits liver fibrosis in a human subject. In an embodiment, the anti-fibrosis agent is an agent that has been approved for clinical use to inhibit liver fibrosis in a human subject.

In certain embodiments, the agent is a candidate anti-fibrosis agent. As used herein, a "candidate anti-fibrosis agent" is an agent believed to have potential as an anti-fibrosis agent but has yet to receive approval for clinical use as an anti-fibrosis agent. In certain embodiments, the candidate anti-fibrosis agent is an agent believed to have potential as an anti-fibrosis agent but has yet to receive approval for clinical use as an anti-fibrosis agent in the treatment of liver fibrosis. In certain embodiments, the candidate anti-fibrosis agent is an agent believed to have potential as an anti-fibrosis agent but has yet to receive approval for clinical use in humans as an anti-fibrosis agent for the treatment of liver fibrosis.

Anti-fibrosis agents and candidate anti-fibrosis agents include, without limitation, interferon alfa-2b, PEG-interferon alfa-2b, PEG-interferon alfa-2a, lamivudine (Epivir), adefovir (Hepsera), telbivudine (Tyzeka), entecavir (Baraclude), ribavirin, boceprivir (Victrelis), telaprevir (Incivek), simeprevir (Olysio), sofosbuvir (Sovaldi), ledipasvir/sofosbuvir (Harvoni), sofosbuvir/velpatasvir, ombitasvir/paritaprevir/ritonavir (Technivie), daclatasvir (Daklinza), dasabuvir, CB1 antagonist (e.g., rimonabant), 5HT-2B receptor antagonist, angiotensin-converting enzyme (ACE) inhibitor, angiotensin II type 1 (AT1) receptor blocker endothelin 1 (ET-1) receptor antagonist, adiponectin, ghrelin, PDGF receptor antagonist, imatinib, nilotinib, tissue inhibitors of metalloproteinases (TIMPs), sulfasalazine, gliotoxin, nonsteroidal anti-inflammatory drugs (NSAIDs), and combination thereof.

In certain embodiments, the agent is selected from the group consisting of interferon alfa-2b, PEG-interferon alfa-2b, PEG-interferon alfa-2a, lamivudine (Epivir), adefovir (Hepsera), telbivudine (Tyzeka), entecavir (Baraclude), ribavirin, boceprivir (Victrelis), telaprevir (Incivek), simeprevir (Olysio), sofosbuvir (Sovaldi), ledipasvir/sofosbuvir (Harvoni), sofosbuvir/velpatasvir, ombitasvir/paritaprevir/ritonavir (Technivie), daclatasvir (Daklinza), dasabuvir, CB1 antagonist (e.g., rimonabant), 5HT-2B receptor antagonist, angiotensin-converting enzyme (ACE) inhibitor, angiotensin II type 1 (AT1) receptor blocker endothelin 1 (ET-1) receptor antagonist, adiponectin, ghrelin, PDGF receptor antagonist, imatinib, nilotinib, tissue inhibitors of metalloproteinases (TIMPs), sulfasalazine, gliotoxin, nonsteroidal anti-inflammatory drugs (NSAIDs), and any combination thereof.

An aspect of the invention is a method of assessing efficacy of an agent for the treatment of liver fibrosis, wherein the agent is selected from the group consisting of anti-fibrosis agents and candidate anti-fibrosis agents, comprising
quantitatively measuring di-sialylated and mono-sialylated O-glycoforms of a peptide fragment of hemopexin in a first test serum sample obtained from a subject, wherein the amino acid sequence of the peptide fragment of hemopexin comprises SEQ ID NO:1;
administering the agent to the subject;
quantitatively measuring di-sialylated and mono-sialylated O-glycoforms of the peptide fragment of hemopexin in a second test serum sample obtained from the subject;
comparing the measured amounts of di-sialylated and mono-sialylated O-glycoforms of the peptide fragment of hemopexin in the first test serum sample to the measured amounts of di-sialylated and mono-sialylated O-glycoforms of the peptide fragment of hemopexin in the second serum sample, wherein the second test serum sample was obtained after the administering and later in time than the first test serum sample; and
identifying the agent as ineffective for treating liver fibrosis when the measured amount of di-sialylated O-glycoform of the peptide fragment of hemopexin in the second test serum sample is increased as compared to corresponding measured amounts in the first test serum sample.

An aspect of the invention is a method of assessing efficacy of an agent for the treatment of liver fibrosis, wherein the agent is selected from the group consisting of anti-fibrosis agents and candidate anti-fibrosis agents, comprising
quantitatively measuring di-sialylated and mono-sialylated O-glycoforms of a peptide fragment of hemopexin in a first test serum sample obtained from a subject, wherein the amino acid sequence of the peptide fragment of hemopexin comprises SEQ ID NO:1;
administering the agent to the subject;
quantitatively measuring di-sialylated and mono-sialylated O-glycoforms of the peptide fragment of hemopexin in a second test serum sample obtained from the subject;
comparing the measured amounts of di-sialylated and mono-sialylated O-glycoforms of the peptide fragment of hemopexin in the first test serum sample to the measured amounts of di-sialylated and mono-sialylated O-glycoforms of the peptide fragment of hemopexin in the second serum sample, wherein the second test serum sample was obtained after the administering and later in time than the first test serum sample; and
identifying the agent as ineffective for treating liver fibrosis when the measured amount of mono-sialylated O-glycoform of the peptide fragment of hemopexin in the second test serum sample is decreased as compared to corresponding measured amounts in the first test serum sample.

An aspect of the invention is a method of assessing efficacy of an agent for the treatment of liver fibrosis, wherein the agent is selected from the group consisting of anti-fibrosis agents and candidate anti-fibrosis agents, comprising
quantitatively measuring di-sialylated and mono-sialylated O-glycoforms of a peptide fragment of hemopexin in a first test serum sample obtained from a subject, wherein the amino acid sequence of the peptide fragment of hemopexin comprises SEQ ID NO:1;
administering the agent to the subject;
quantitatively measuring di-sialylated and mono-sialylated O-glycoforms of the peptide fragment of hemopexin in a second test serum sample obtained from the subject;
comparing the measured amounts of di-sialylated and mono-sialylated O-glycoforms of the peptide fragment of hemopexin in the first test serum sample to the measured amounts of di-sialylated and mono-sialylated O-glycoforms of the peptide fragment of hemopexin in the second serum sample, wherein the second test serum sample was obtained after the administering and later in time than the first test serum sample; and identifying the agent as ineffective for treating liver fibrosis when the measured amount of di-sialylated O-glycoform of the peptide fragment of hemopexin in the second test serum sample is increased, and the measured amount of mono-sialylated O-glycoform of the peptide fragment of hemopexin in the second test serum sample is decreased, as compared to corresponding measured amounts in the first test serum sample.

In certain embodiments, the amino acid sequence of the peptide fragment of hemopexin consists of SEQ ID NO:1.

In certain embodiments, the measuring comprises LC-MS/MS-MRM (liquid chromatography/tandem mass spectrometry/multiple reaction monitoring), as described herein.

In certain embodiments, the measuring comprises LC/MS3 (liquid chromatography with triple-stage mass spectrometric detection), as described herein.

An aspect of the invention is a method of treating liver fibrosis, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the subject, wherein the reference serum sample was obtained earlier in time than the test serum sample;

identifying the subject as having increased liver fibrosis when the measured amount of di-sialylated O-glycoform of the peptide fragment of hemopexin in the test serum sample is increased as compared to corresponding measured amounts in the reference serum sample; and administering to the subject having increased liver fibrosis an initial amount or an increased amount of an anti-fibrosis agent.

An aspect of the invention is a method of treating liver fibrosis, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the subject, wherein the reference serum sample was obtained earlier in time than the test serum sample;

identifying the subject as having increased liver fibrosis when the measured amount of measured amount of mono-sialylated O-glycoform of the peptide fragment of hemopexin in the test serum sample is decreased as compared to corresponding measured amounts in the reference serum sample; and administering to the subject having increased liver fibrosis an initial amount or an increased amount of an anti-fibrosis agent.

An aspect of the invention is a method of treating liver fibrosis, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the subject, wherein the reference serum sample was obtained earlier in time than the test serum sample;

identifying the subject as having increased liver fibrosis when the measured amount of di-sialylated O-glycoform of the peptide fragment of hemopexin in the test serum sample is increased, and the measured amount of mono-sialylated O-glycoform of the peptide fragment of hemopexin in the test serum sample is decreased, as compared to corresponding measured amounts in the reference serum sample; and administering to the subject having increased liver fibrosis an initial amount or an increased amount of an anti-fibrosis agent.

In certain embodiments, the amino acid sequence of the peptide fragment of hemopexin consists of SEQ ID NO:1.

In certain embodiments, the measuring comprises LC-MS/MS-MRM (liquid chromatography/tandem mass spectrometry/multiple reaction monitoring), as described herein.

In certain embodiments, the measuring comprises LC/MS3 (liquid chromatography with triple-stage mass spectrometric detection), as described herein.

In certain embodiments, the subject having increased liver fibrosis is naïve to anti-fibrosis treatment and is administered an initial amount of the anti-fibrosis agent.

In certain embodiments, the subject having increased liver fibrosis is already receiving anti-fibrosis treatment and is administered an increased amount of the anti-fibrosis agent.

In certain embodiments, the anti-fibrosis agent is selected from the group consisting of interferon alfa-2b, PEG-interferon alfa-2b, PEG-interferon alfa-2a, lamivudine (Epivir), adefovir (Hepsera), telbivudine (Tyzeka), entecavir (Baraclude), ribavirin, boceprivir (Victrelis), telaprevir (Incivek), simeprevir (Olysio), sofosbuvir (Sovaldi), ledipasvir/sofosbuvir (Harvoni), sofosbuvir/velpatasvir, ombitasvir/paritaprevir/ritonavir (Technivie), daclatasvir (Daklinza), dasabuvir, CB1 antagonist (e.g., rimonabant), 5HT-2B receptor antagonist, angiotensin-converting enzyme (ACE) inhibitor, angiotensin II type 1 (AT1) receptor blocker endothelin 1 (ET-1) receptor antagonist, adiponectin, ghrelin, PDGF receptor antagonist, imatinib, nilotinib, tissue inhibitors of metalloproteinases (TIMPs), sulfasalazine, gliotoxin, non-steroidal anti-inflammatory drugs (NSAIDs), and any combination thereof.

An aspect of the invention is a method of treating liver fibrosis, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the test subject, wherein the reference serum sample was obtained earlier in time than the test serum sample;

identifying the test subject as having decreased liver fibrosis when the measured amount of di-sialylated O-glycoform of the peptide fragment of hemopexin in the test serum sample is decreased as compared to corresponding measured amounts in the reference serum sample; and administering to the subject having decreased liver fibrosis a continued amount or a decreased amount of an anti-fibrosis agent.

An aspect of the invention is a method of treating liver fibrosis, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the test subject, wherein the reference serum sample was obtained earlier in time than the test serum sample;

identifying the test subject as having decreased liver fibrosis when the measured amount of mono-sialylated O-glycoform of the peptide fragment of hemopexin in the test serum sample is increased as compared to corresponding measured amounts in the reference serum sample; and administering to the subject having decreased liver fibrosis a continued amount or a decreased amount of an anti-fibrosis agent.

An aspect of the invention is a method of treating liver fibrosis, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the test subject, wherein the reference serum sample was obtained earlier in time than the test serum sample;

identifying the test subject as having decreased liver fibrosis when the measured amount of di-sialylated O-glycoform of the peptide fragment of hemopexin in the test serum sample is decreased, and the measured amount of mono-sialylated O-glycoform of the peptide fragment of hemopexin in the test serum sample is increased, as compared to corresponding measured amounts in the reference serum sample; and administering to the subject having decreased liver fibrosis a continued amount or a decreased amount of an anti-fibrosis agent.

In certain embodiments, the amino acid sequence of the peptide fragment of hemopexin consists of SEQ ID NO:1.

In certain embodiments, the measuring comprises LC-MS/MS-MRM (liquid chromatography/tandem mass spectrometry/multiple reaction monitoring), as described herein.

In certain embodiments, the measuring comprises LC/MS3 (liquid chromatography with triple-stage mass spectrometric detection), as described herein.

In certain embodiments, the subject having decreased liver fibrosis is already being treated with an anti-fibrosis agent and is administered a continued amount of the anti-fibrosis agent. For example, in certain embodiments, the subject having decreased liver fibrosis is already being treated with a first amount of an anti-fibrosis agent, and, based on the measuring, comparing, and identifying, is administered a continued first amount of the anti-fibrosis agent.

In certain embodiments, the subject having decreased liver fibrosis is already being treated with an anti-fibrosis agent and is administered a decreased amount of the anti-fibrosis agent. For example, in certain embodiments, the subject having decreased liver fibrosis is already being treated with a first amount of an anti-fibrosis agent, and, based on the measuring, comparing, and identifying, is administered a decreased amount of the anti-fibrosis agent, wherein the decreased amount is less than the first amount.

In certain embodiments, the anti-fibrosis agent is selected from the group consisting of interferon alfa-2b, PEG-interferon alfa-2b, PEG-interferon alfa-2a, lamivudine (Epivir), adefovir (Hepsera), telbivudine (Tyzeka), entecavir (Baraclude), ribavirin, boceprivir (Victrelis), telaprevir (Incivek), simeprevir (Olysio), sofosbuvir (Sovaldi), ledipasvir/sofosbuvir (Harvoni), sofosbuvir/velpatasvir, ombitasvir/paritaprevir/ritonavir (Technivie), daclatasvir (Daklinza), dasabuvir, CB1 antagonist (e.g., rimonabant), 5HT-2B receptor antagonist, angiotensin-converting enzyme (ACE) inhibitor, angiotensin II type 1 (AT1) receptor blocker endothelin 1 (ET-1) receptor antagonist, adiponectin, ghrelin, PDGF receptor antagonist, imatinib, nilotinib, tissue inhibitors of metalloproteinases (TIMPs), sulfasalazine, gliotoxin, non-steroidal anti-inflammatory drugs (NSAIDs), and any combination thereof.

EXAMPLES

Study Population

The initial discovery of O-glycoforms of HPX associated with liver disease progression was carried out using samples of HCC patients (n=10), cirrhotic patients (n=10), and healthy individuals (n=10) enrolled in collaboration with the Department of Hepatology and Liver Transplantation, Georgetown University Hospital, Washington, D.C. under protocols approved by the Institutional Review Board. Briefly, all patients (HCC and cirrhosis) selected for this study had chronic HCV infection as primary diagnosis and all the HCC participants had stage 1 and 2 tumors according to the 7th edition of the American Joint Committee on Cancer Staging manual. Blood samples were collected using EDTA Vacutainer tubes (BD Diagnostics, Franklin Lakes, N.J.); plasma was collected according to the manufacturer's protocol and stored at −80° C. until use. Participants were split into groups of 5 and plasma was pooled for analysis (2 pools per group, 5 participants per pool). All the groups were matched on age, race (60% Caucasian, 40% African-American), and gender (80% males). HCC and cirrhosis groups were further matched on MELD (model for end-stage liver disease) score as previously described. Comunale et al., *PLoS ONE* 5(8): e12419 (2010).

Further serum samples were provided by NIDDK from the HALT-C trial, a prospective randomized controlled trial of 1,050 patients that evaluated effect of long-term low-dose PEG-interferon alpha-2a in participants that failed initial anti-HCV therapy with interferon. Di Bisceglie et al., *N Engl J Med* 359: 2429-2441 (2008); Lok et al., *Hepatology* 49: 1828-1837 (2009). A total of 114 participants (76 liver disease patients from the HALT-C trial and 38 disease-free controls recruited at Georgetown University) were included in the analysis (Table 1).

TABLE 1

Basic characteristics of disease-free controls and groups of the HALT-C participants [a]

|  | Healthy | Fibrosis | Cirrhosis | p-value [b] |
|---|---|---|---|---|
| N | 38 | 37 | 39 | n/a |
| male [%] | 68 | 59 | 72 | 0.502 |
| race (CA/AA) | 20/12 [c] | 30/7 | 28/11 | 0.106 |
| age (years) | 49.3 ± 7.7 | 50.1 ± 7.1 | 50.9 ± 6.5 | 0.614 |
| IFN treatment (yes/no) | n/a | 13/24 | 12/27 | 0.686 |
| ALT [U/L] | n/a | 89.1 ± 41.3 | 129.7 ± 69.5 | 0.007 |
| AST [U/L] | n/a | 67.4 ± 25.6 | 110.0 ± 65.0 | 0.002 |
| platelet ($10^9$/L) | n/a | 191.2 ± 59.4 | 144.7 ± 57.4 | <0.001 |
| albumin [g/dL] | n/a | 4.0 ± 0.3 | 3.8 ± 0.4 | 0.115 |
| AFP [ng/mL] | n/a | 11.7 ± 14.7 | 22.9 ± 24.6 | 0.005 |
| alkaline phosphatase [U/L] | n/a | 91.7 ± 29.6 | 123.6 ± 52.1 | 0.636 |
| INR | n/a | 1.0 ± 0.1 | 1.1 ± 0.1 | <0.001 |
| bilirubin [mg/dL] | n/a | 0.7 ± 0.4 | 0.9 ± 0.4 | 0.039 |
| creatinine [mg/dL] | n/a | 0.8 ± 0.1 | 0.9 ± 0.2 | 0.936 |
| MELD | n/a | 6.8 ± 1.3 | 7.5 ± 1.4 | 0.006 |
| APRI | n/a | 0.9 ± 0.5 | 2.4 ± 2.5 | <0.001 |
| FIB-4 | n/a | 2.1 ± 1.1 | 3.5 ± 2.7 | <0.001 |

[a] Values are expressed as mean ± standard deviation.
[b] p-value was calculated using Mann-Whitney U test or Kruskal-Wallis test for quantitative variables and chi-square test for categorical variables.
[c] Six healthy controls belong to the Hispanic ethnic group.

Liver disease status of the HALT-C participants was classified based on biopsy-evaluation into fibrosis (Ishak score 3-4, n=37) or cirrhosis (Ishak score 5-6, n=39) groups. To minimize classification error, patients were selected with consistent Ishak scores at three biopsy measurements at month 0, 24, and 48 after randomization. However, two fibrotic participants with Ishak score 3 had only one biopsy and 7 participants (3 cirrhotic and 4 fibrotic) crossed disease categories at one biopsy time point. For those participants, blood samples collected at a time point closest to the disease outcome consistent with their group assignment were analyzed. The two groups of liver disease participants and the controls were matched on age and gender. The disease-free participants donated blood samples at four successive visits in the span of one year and answered a brief questionnaire inquiring about basic demographic information and medical history. The study groups were further divided into Discovery (23 disease-free controls, 23 fibrotic, and 24 cirrhotic) and Verification (15 disease-free controls, 15 fibrotic, and 15 cirrhotic) sets of participants (Table 2). The fibrosis and cirrhosis groups in the Discovery set consisted of similar proportions of participants from the IFN treatment and control arms of the HALT-C trial; the Verification set consisted of participants from the control arm.

TABLE 2

Basic characteristics of disease-free controls and HALT-C participants [a]

|  | Healthy | Fibrosis | Cirrhosis | p-value [b] |
|---|---|---|---|---|
| Discovery |  |  |  |  |
| N | 23 | 22 | 24 | n/a |
| male [%] | 65 | 50 | 71 | 0.326 |
| race (CA/AA) | 8/9 [c] | 18/4 | 16/8 | 0.019 |
| age (years) | 48.4 ± 9.2 | 51.0 ± 7.5 | 50.3 ± 7.5 | 0.578 |
| IFN treatment (yes/no) | n/a | 13/9 | 12/12 | 0.536 |
| ALT [U/L] | n/a | 102.7 ± 66.8 | 122 ± 71.8 | 0.231 |
| AST [U/L] | n/a | 72.9 ± 35.5 | 109.6 ± 77.3 | 0.126 |
| platelet ($10^9$/L) | n/a | 196.4 ± 55.4 | 143.3 ± 66.0 | <0.001 |
| albumin [g/dL] | n/a | 4.0 ± 0.4 | 3.6 ± 0.5 | 0.016 |
| AFP [ng/mL] | n/a | 9.7 ± 12.0 | 20.1 ± 16.8 | 0.002 |
| alkaline phosphatase [U/L] | n/a | 81 ± 33 | 131 ± 92 | 0.553 |
| INR | n/a | 1.0 ± 0.1 | 1.2 ± 0.2 | <0.001 |
| bilirubin [mg/dL] | n/a | 0.8 ± 0.6 | 1.3 ± 0.8 | 0.057 |
| creatinine [mg/dL] | n/a | 0.9 ± 0.3 | 0.9 ± 0.3 | 0.301 |
| MELD | n/a | 7.6 ± 2.2 | 10.0 ± 2.9 | 0.009 |
| APRI | n/a | 0.9 ± 0.5 | 2.6 ± 2.8 | 0.004 |
| FIB-4 | n/a | 1.7 ± 0.6 | 3.66 ± 3.12 | 0.006 |
| Validation |  |  |  |  |
| N | 15 | 15 | 15 | n/a |
| male [%] | 73 | 67 | 73 | 0.993 |
| race (CA/AA) | 12/3 | 12/3 | 12/3 | n/a |
| age (years) | 50.6 ± 4.8 | 48.3 ± 6.8 | 51.5 ± 4.7 | 0.281 |
| IFN treatment (yes/no) | n/a | 0/15 | 0/15 | n/a |
| ALT [U/L] | n/a | 81.4 ± 32.5 | 133 ± 90.7 | 0.169 |
| AST [U/L] | n/a | 64.4 ± 25.3 | 110 ± 58.5 | 0.040 |
| platelet ($10^9$/L) | n/a | 179 ± 57.3 | 153 ± 36.2 | 0.266 |
| albumin [g/dL] | n/a | 4.0 ± 0.4 | 3.9 ± 0.4 | 0.616 |
| AFP [ng/mL] | n/a | 13.3 ± 17.1 | 26.3 ± 33.5 | 0.396 |
| alkaline phosphatase [U/L] | n/a | 94 ± 26 | 104 ± 60 | 0.967 |
| INR | n/a | 1.0 ± 0.1 | 1.0 ± 0.1 | 0.129 |
| bilirubin [mg/dL] | n/a | 0.7 ± 0.3 | 0.8 ± 0.4 | 0.595 |
| creatinine [mg/dL] | n/a | 0.8 ± 0.2 | 0.9 ± 0.2 | 0.416 |
| MELD | n/a | 6.3 ± 0.6 | 7.3 ± 1.5 | 0.012 |
| APRI | n/a | 0.1 ± 0.6 | 1.8 ± 1.2 | 0.050 |
| FIB-4 | n/a | 2.2 ± 1.3 | 3.4 ± 1.4 | 0.050 |

[a] Values are expressed as mean ± standard deviation.
[b] p-value was calculated using Mann-Whitney U test or Kruskal-Wallis test for quantitative variables and chi-square test for categorical variables.
[c] Six healthy controls belong to the Hispanic ethnic group.

Example 1

Isolation of HPX and Separation of Glycopeptides by HILIC Chromatography

HPX was purified from plasma by hemin affinity followed by C18 chromatography as previously described. Sanda et al., *Electrophoresis* 34: 2342-2349 (2013). Isolated HPX (20 pmol), dried in a vacuum concentrator and stored at −80° C., was suspended in 50 mM ammonium bicarbonate solution, pH 7.8 (Sigma-Aldrich, St. Louis, Mo.) with 0.05% RapiGest (Waters, Milford, Mass.), reduced, alkylated, and digested with 0.2 μg of Trypsin Gold for MS (Promega, Madison, Wis.) in a Barocycler reactor (Pressure BioSciences, South Easton, Mass.) at 37° C. for 60 minutes, also as previously described. O-glycopeptides were isolated by hydrophilic interaction chromatography (HILIC) on a ZIC- HILIC column 150×2.1 mm, 3 µm particles (EMD Merck, Germany) in a 30 min HPLC (Agilent, Santa Clara, Calif.) gradient of acetonitrile (ACN)/H$_2$O with 0.01% trifluoroacetic acid (TFA). Starting conditions were set to 90% ACN with 0.01% TFA followed by 30 min gradient elution to 90% of H$_2$O with 0.01% TFA. Peptides were monitored at 214 and 280 nm using a DAD detector (Agilent Technologies, Santa Clara, Calif.). Glycopeptide fractions were collected and dried on a vacuum concentrator (Labconco, Kansas City, Mo.) for further use.

Example 2

De-Sialylation and Exoglycosidase Treatment of O-Glycopeptides of HPX

Tryptic digest of HPX or the HILIC-enriched glycopeptide fractions of the tryptic digest were de-sialylated with 2 M acetic acid (Sigma-Aldrich) at 80° C. Completion of the de-sialylation reaction was confirmed by LC-MS/MS analysis. De-sialylated glycopeptides were evaporated in a vacuum concentrator (Labconco) and further treated with 0.1 U of 1-3 beta galactosidase (New England BioLabs, Ipswich, Mass.) in 50 mM sodium acetate, pH 6, at 37° C. for 8 hours. Products of the reaction were cleaned for further analysis by SPE C18, concentrated using vacuum concentrator, and dissolved in 0.1% formic acid for further LC-MS analysis.

Example 3

LC-MS/MS Analysis

Tryptic digest of HPX, HILIC-enriched fractions, or acid- and exoglycosidase-treated glycopeptide fractions were analyzed under identical chromatographic conditions. Peptides were separated by reversed phase chromatography (Tempo Eksigent-AB Sciex, Framingham, Mass.) on a ChromXP C18-CL (3 µm, 120 Å, 180 µm, 20 mm) trap column and ChromXP C18-CL (3 µm, 120 Å, 75 µm, 150 mm) HPLC capillary chip column (Eksigent-AB Sciex) interfaced with a 5600 TripleTOF mass spectrometer (AB Sciex, Framingham, Mass.). Chromatographic method consisted of 10-min trapping/washing step (2% ACN, 0.1% formic acid (FA)) at 3 µL/min flow rate and 30 min gradient elution at a flow rate of 300 nL/min (Solvent A: 2% ACN with 0.1% FA; Solvent B: 100% ACN with 0.1% FA) using the following timetable: 5-40% Solvent B 0-23 min; 45-100% Solvent B 23-25 min; 100% Solvent B 25-30 min. Mass spectrometer was set to ion spray voltage 2,400 V, ion source gas (GS1) 13, declustering potential 90 and interface heater temperature 150° C., and operated in data-dependent mode; each survey scan (m/z 400 to 1,600) was followed by MS/MS on 25 precursor ions in the range m/z 100-1,800, with the dynamic exclusion time set to 6 sec, and 150 counts threshold for two repeated precursors. Collision energy was set automatically according to charge state and m/z of precursor ion. Data dependent analysis was used to identify major glycoforms and precursor extracted ion chromatogram (XIC) of 0.05 Da window was used to evaluate changes in glycoform quantities in liver disease (cirrhosis and HCC). Glycopeptide intensities were normalized to an internal tryptic peptide of HPX to eliminate influence of changes in the concentration of HPX protein on the quantitative outcome.

Example 4

LC/MS3 and LC-MS/MS-MRM Analysis of O-Glycopeptides of HPX

Studies of S-HPX in serum of patients were done directly without enrichment of HPX. Serum samples (2 µL) were diluted in 140 µL of 25 mM NH$_4$HCO$_3$ with 0.1% RapiGest (Waters), reduced by 5 mM dithiothreitol (DTT) for one hour at 60° C., and alkylated with 15 mM iodoacetamide (IAA) for 20 min at room temperature (RT) in the dark. Residual IAA was reduced with 5 mM DTT for 20 min at RT. Reduced and alkylated samples (20 µL) were digested with trypsin in a Barocycler reactor as described above. Tryptic peptides were analyzed on a NanoAcquity UPLC (Waters) by RP chromatography on a Symmetry C18 (3 µm, 180 µm, 20 mm) trap column and UPLC capillary column (BEH 300 Å, 1.7 µm, 150 mm×0.75 µm) (Waters) interfaced with a 6500 QTRAP mass analyzer (AB Sciex). Separation was achieved by a 60 min gradient elution with ACN containing 0.1% formic acid (B) starting from 2% ACN with 0.1% formic acid (A) (0-1 min 99% A, 1-20 min 99-50% A, 20-38 min 50-2% A, 38-45 min 2% A, 45-45.5 min 2-99% A, 45.5-60 min 99% A). Ion source parameters were set to declustering potential 80 V, curtain gas 20, ion spray voltage 2,400 V, ion source gas 1 22, interface heater 180° C., entrance potential 10 V, collision exit potential 13 V. Directly compared were (i) the MS/MS-MRM monitoring (843.9→905.6) transition for monosialo-T and (916.7→905.6) transition for disialo-T structure and (ii) MS3 monitoring 3 product ions (m/z: 504.1, 716.3 and 802.5) in the ion trap MS3 spectra with window width 3 Da; these three peptide backbone fragments derive from the peptide ion obtained in MS2 of the respective glycopeptide precursor ions as previously described. Ion trap scan time of 2000 Da/s, Q0 trapping and 20 ms fixed linear ion trap fill time were used for the MS3 method. A QC sample (one control serum sample) was prepared as described above and injected once per two sample injections in order to evaluate method stability and reproducibility. Data analysis was carried out using MultiQuant software 2.1 (AB Sciex).

Example 5

Statistical Analysis

S-HPX, the ratio of di-sialylated (NeuAc$_2$Hex$_1$HexNAc$_1$) to mono-sialylated (NeuAc$_1$Hex$_1$HexNAc$_1$) glycoforms of the peptide TPLPPTSAHGNVAEGETKPDPVTER (SEQ ID NO:1) of HPX carrying one O-glycan on the T1, was used as a final quantitative measure for evaluation of liver disease. S-HPX in the disease-free controls (n=38) was compared to the fibrosis (n=37) and cirrhosis (n=39) groups of participants in the HALT-C trial divided into and verification sample sets. All samples were blinded to the analyst and randomized in order of analysis. Descriptive statistics of participants within the three disease groups are summarized in Table 1; chi-square tests were used for categorical variables and Mann-Whitney U test or Kruskal-Wallis test were for quantitative variables. S-HPX between the three disease groups in the Discovery set (FIG. 3A), S-HPX between four different blood draws in the disease-free controls (FIG. 3B), and influence of IFN treatment on S-HPX (Table 3) were analyzed using Mann-Whitney U test or Kruskal-Wallis due to non-normality of S-HPX values. Logistic regression models were used to evaluate the association between S-HPX and liver disease status in the Discovery set. Disease status was the dependent variable and S-HPX was the main independent variable; other clinical variables including alpha fetoprotein (AFP) and platelet count were used as independent variables. Optimal cut-off point for each independent variable was determined by maximizing sensitivity and specificity. The performance of S-HPX and other variables in classification of liver disease was assessed using area under the receiver operating characteristic curve (AuROC) analysis in the Verification set using the cut-off points derived from the Discovery set (Table 4). All reported p-values are two sided. Statistical analyses were performed using SAS v 9.4 (SAS Institute, Cary, N.C.).

TABLE 3

Impact of IFN treatment on S-HPX. Groups of fibrotic (FIB) and cirrhotic (CIR) participants in the HALT-C trial were separated into IFN-treated and control arms.

| Group (N) | IFN | Mean ± SD | Median (Min, Max) | p-value |
|---|---|---|---|---|
| FIB (13) | yes | 20.9 ± 8.1 | 20.6 (11.0, 41.3) | 0.161 |
| FIB (9) | no | 30.7 ± 19.1 | 25.0 (13.8, 76.0) | |
| CIR (12) | yes | 55.4 ± 30.0 | 48.0 (19.5, 106.5) | 0.157 |
| CIR (12) | no | 81.7 ± 42.7 | 78.8 (22.1, 156.1) | |

TABLE 4

ROC models comparing influence of clinical variables determined at baseline visit on separation of the fibrosis and cirrhosis groups in the Validation set[a].

| | Cut-off point[b] | Sensitivity (%) | Specificity (%) | St. AuROC | Error | 95% CI |
|---|---|---|---|---|---|---|
| AFP | 11.6 | 50 | 79 | 0.65 | 0.153 | (0.35, 0.95) |
| Platelet | 163 | 80 | 50 | 0.63 | 0.134 | (0.37, 0.89) |
| APRI | 1.45 | 60 | 86 | 0.73 | 0.145 | (0.44, 1.00) |
| FIB-4 | 2.60 | 80 | 71 | 0.74 | 0.144 | (0.47, 1.00) |
| S-HPX | 42.5 | 60 | 93 | 0.84 | 0.145 | (0.53, 1.00) |

Figure 4A:
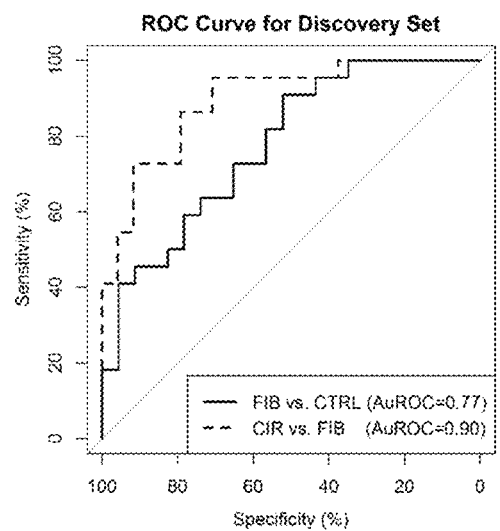
FIG. 4A is a graph depicting ROC (receiver operating characteristics) curve analysis of progressing liver disease. Shown are ROC curves comparing the following groups based on measurement of S-HPX: Discovery Set: fibrosis (FIB, n=22) vs. control (CTRL, n=23) and cirrhosis (CIR, n=24) vs. fibrosis (FIB, n=22).
Figure 4B:
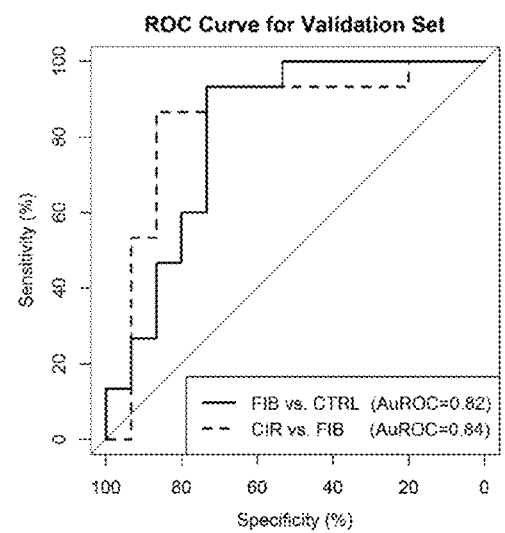
FIG. 4B is a graph depicting ROC (receiver operating characteristics) curve analysis of progressing liver disease. Shown are ROC curves comparing the following groups based on measurement of S-HPX: Validation Set: fibrosis (FIB, n=15) vs. control (CTRL, n=15) and cirrhosis (CIR, n=15) vs. fibrosis (FIB, n=15).

[a]Samples were used in FIG. 4B.
[b]Optimal cut-off point was calculated based on fitted models from the Discovery set.

Example 6

O-Glycopeptides of HPX in Liver Disease

Plasma samples from disease-free controls and cirrhotic patients (CIR) with or without HCC provided a baseline for the examination of O-glycoforms of HPX detectable in liver disease. HPX was isolated by hemin affinity and C18 HPLC from the pooled plasma of participants as described in the examples above. The yield of HPX, purified to greater than 95% purity, was 20-25 µg per 100 µL of plasma. Glycopeptides of HPX were enriched by HILIC chromatography (FIG. 1) and analyzed by LC-MS/MS as previously described in [12,17]. Sanda et al., *Electrophoresis* 34: 2342-2349 (2013). Combined analysis of all the pools led to the identification of fifteen (15) O-glycopeptides of HPX (Table 5) derived from the N-terminal tryptic peptide of HPX, TPLPPTSAHGNVAEGETKPDPVTER (SEQ ID NO:1).

TABLE 5

Detected glycan compositions of the TPLPPTSAHGNVAEGETKPDPVTER (SEQ ID NO: 1) O-glycopeptides in tryptic digest of hemopexin isolated from pooled plasma of disease-free controls, cirrhotic, and HCC patients. Relative abundance is estimated as percent XIC signal of each glycopeptide (m/z) normalized to the sum of all O-glycopeptides.

| m/z | glycan composition | XIC % |
|---|---|---|
| 973.1(3+) | HexNAc | 0.35 |
| 770.8(4+) | HexNAc-Gal | 1.74 |
| 843.6(4+) | HexNAc-Gal-Neu5Ac | 66.19 |
| 916.4(4+) | HexNAc-Gal-2Neu5Ac | 19.61 |
| 894.4(4+) | 2HexNAc-Gal-Neu5Ac | 0.16 |
| 934.8(4+) | 2HexNAc-2Gal-Neu5Ac | 0.38 |
| 1007.7(4+) | 2HexNAc-2Gal-2Neu5Ac | 7.22 |
| 1080.5(4+) | 2HexNAc-2Gal-3Neu5Ac | 1.62 |
| 1153.3(4+) | 2HexNAc-2Gal-4Neu5Ac | 0.68 |
| 1058.2(4+) | 3HexNAc-2Gal-2Neu5Ac | 0.09 |
| 1099.2(4+) | 3HexNAc-3Gal-2Neu5Ac | 0.15 |
| 937.6(5+) | 3HexNAc-3Gal-3Neu5Ac | 1.23 |
| 995.8(5+) | 3HexNAc-3Gal-4Neu5Ac | 0.45 |
| 1054.1(5+) | 3HexNAc-3Gal-5Neu5Ac | 0.08 |
| 1112.3(5+) | 3HexNAc-3Gal-6Neu5Ac | 0.04 |

Figure 1:
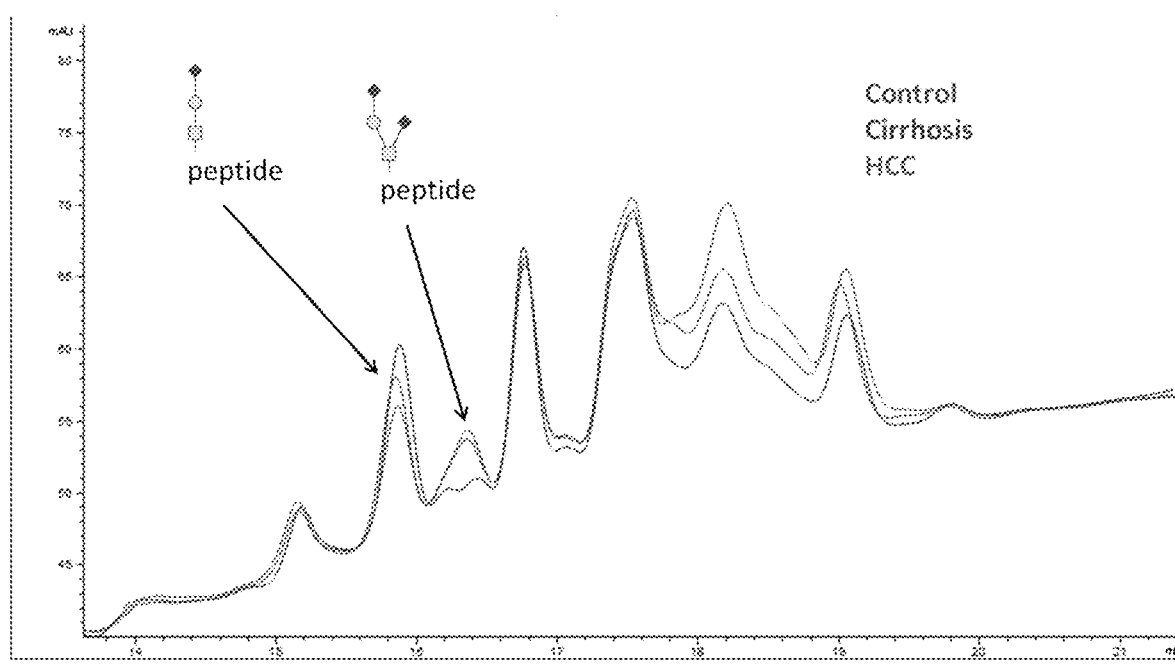
FIG. 1 is a graph depicting peaks of O-glycopeptides of a tryptic digest of hemopexin (HPX) separated by hydrophilic interaction chromatography (HILIC). Curves correspond to plasma from control, cirrhosis, and HCC (hepatocellular carcinoma) subjects. The peaks indicated by arrows represent the mono-sialylated core 1 O-glycopeptide (RT 15.9 min, m/z 843.6) followed by the di-sialylated core 1 O-glycopeptide (RT 16.4 min, m/z 916.4).

Other O-glycosylated peptides of HPX were not observed in any of the samples. Estimates of the abundance of these O-glycoforms, based on intensities of precursor ions in the LC-MS/MS scans, showed that two glycoforms (mono-sialylated HexNAc-Gal-Neu5Ac, 66% total intensity; and di-sialylated HexNAc-Gal-2Neu5Ac, 20% total intensity) dominated the distribution. These two glycoforms were also clearly visible in the HILIC chromatograms by UV-Vis detection (FIG. 1). The chromatogram shows that the doubly sialylated glycoform (HexNAc-Gal-2Neu5Ac) increases in cirrhosis and HCC samples compared to disease-free controls while the mono-sialylated O-glycoform (HexNAc-Gal-Neu5Ac) decreases. Major contribution of the above glycoforms to these isolated peaks was confirmed by LC-MS/MS analysis. Further analysis of the precursor ion peak-intensities in XIC of the LC-MS data confirmed the trend towards increased sialylation of the O-glycoforms of HPX in liver disease (FIG. 2). The results show an approximately 4-fold increase in di-sialylated O-glycopeptide of HPX in cirrhosis and further increase in the cirrhotics with HCC with a simultaneous approximately 20% decrease in the mono-sialylated O-glycopeptide of HPX. The changes were quite consistent in measurements of two independent pools of samples per group. FIG. 2 also shows that the minor O-glycoforms (2HexNAc-2Gal-2Neu5Ac and 2HexNAc-2Gal-3Neu5Ac), which are about 10 times less intense, showed a similar trend towards increased sialylation in the liver disease context.

Figure 5:
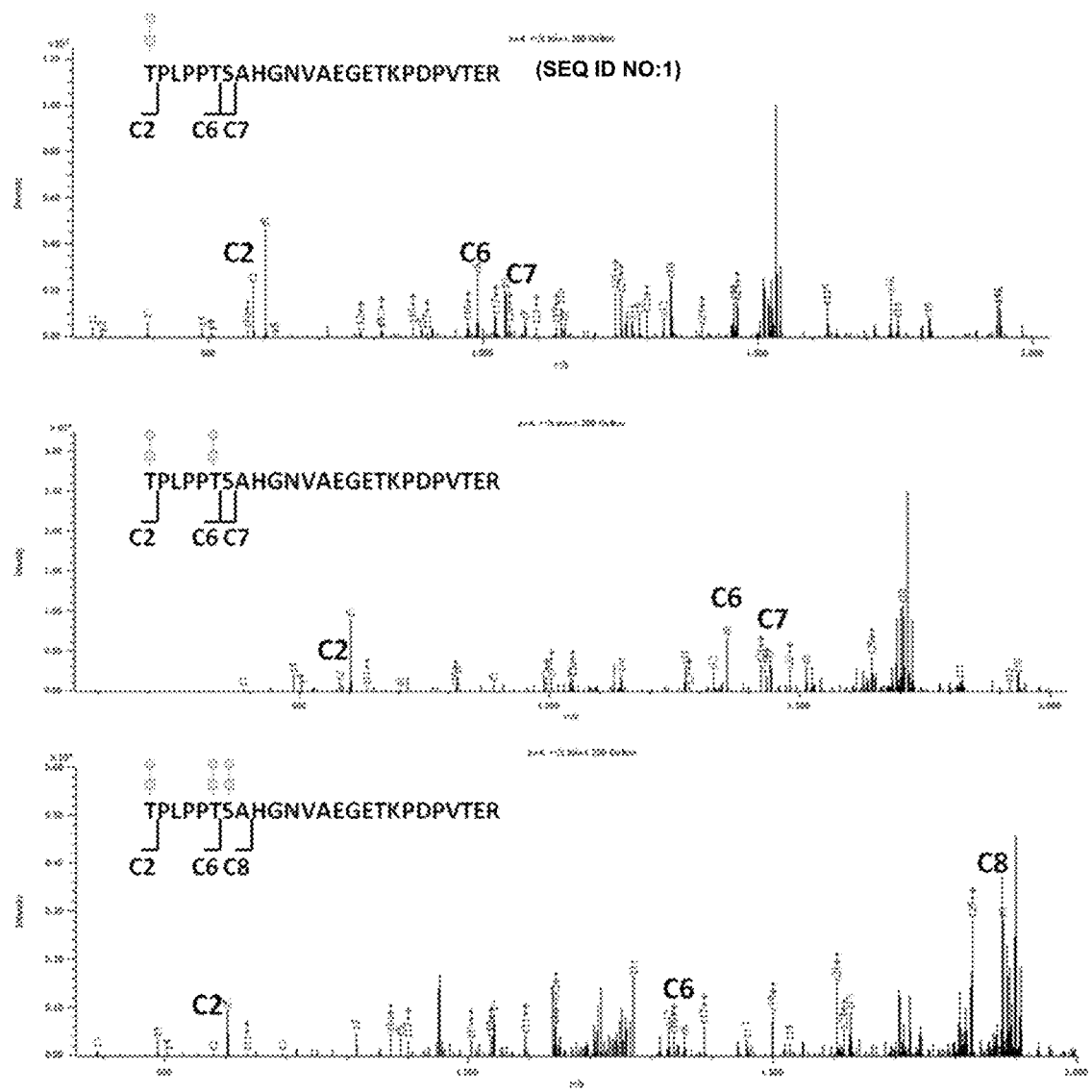
FIG. 5 is three ETD spectra of sialidase-treated O-glycopeptides corresponding to HILIC fractions of mono-(top), bis-(middle), and triply-(bottom) glycosylated O-glycopeptide of HPX. The labeled fragments (C2, C3, C6, C7 and C8) define unequivocally the sites occupied by O-glycans.

LC-ETD/MS analysis of the enriched glycopeptides was carried out to understand whether the minor glycoforms represent large O-glycans attached to a single site or smaller O-glycans attached to several serines (S) or threonines (T) in the peptide sequence. This technique allows fragmentation of the peptide backbone with preservation of the peptide-glycan bond which allows determination of sites occupied by the O-glycans. To further increase efficiency of the analysis, the glycopeptides were labeled with mTRAQ reagent which increased charge state of the labeled peptides to (4+) and improved ETD fragmentation compared to the unlabeled glycopeptide in charge state (3+). Analysis was further optimized by removal of sialic acids from the microheterogeneous peptide population by treatment with acetic acid which improved recovery of the informative fragments (FIG. 5). The analysis confirms that smaller O-glycans were observed on multiple serines/threonines. Glycosylation was observed on serine or threonine other than T1 only when T1 is occupied, which shows that O-glycosylation of this peptide starts from the N-terminus and progresses to additional sites in the C-terminal direction. The additional sites are modified to a lesser degree than the T1 site. Fragmentation of the peptide shown in FIG. 5 documents that position T1 and T6 are occupied in case of doubly glycosylated peptide; triply glycosylated peptide is occupied at position T1, T6, and S7. This was further confirmed by the lack of larger glycans in the analysis of permethylated O-glycans detached by beta elimination (data not shown).

Example 7

Analysis of S-HPX in Serum Samples of the HALT-C Trial Participants

Mono- and di-sialylated core-1 mucin type O-glycans attached to the T1 position of the N-terminal tryptic peptide of HPX are the dominant liver-secreted glycoforms (Table 5). These two glycoforms change substantially in liver disease (FIG. 1) with several-fold increase in the di-sialylated O-glycoform of HPX and simultaneous approximately 20% decrease in the mono-sialylated O-glycoform of HPX (FIG. 2). Thus the ratio of these two major glycoforms, termed S-HPX, is a quantitative measure for assessment of liver disease by the targeted LC/MS3 or LC-MS/MS-MRM assays described herein. Quantification of S-HPX was applied to serum samples of participants in the HALT-C trial (n=76) and to disease-free controls (n=38). As expected, the clinical variables including ALT, AST, bilirubin, INR, albumin, AFP, and platelet count differed significantly between the fibrosis and cirrhosis groups (Table 1). Likewise, the calculated MELD score, APRI (AST-to-platelet ratio index), and FIB-4 (fibrosis-4 index) differed significantly between these two groups. The participants were further divided into Discovery (23 disease-free controls, 22 fibrosis, 24 cirrhosis) and Verification (n=15 each of the three groups) sets of samples (Table 2).

Figure 3A:
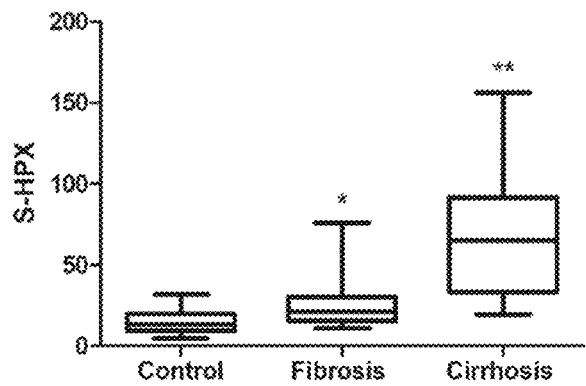
FIG. 3A is a graph depicting direct quantification of the ratio (S-HPX) of di-sialylated to mono-sialylated glycoforms of the peptide TPLPPTSAHGNVAE-GETKPDPVTER (SEQ ID NO:1) of HPX at progressing stages of liver disease. Shown are data for disease-free controls (n=23), liver fibrosis (n=22), and cirrhosis (n=24) patients. The box and whisker plots represents median, $25^{th}$-$75^{th}$ percentile, range of values, and outliers. *, significantly different at p<0.01 from control; **, significantly different at p<0.01 from the fibrosis group.
Figure 3B:
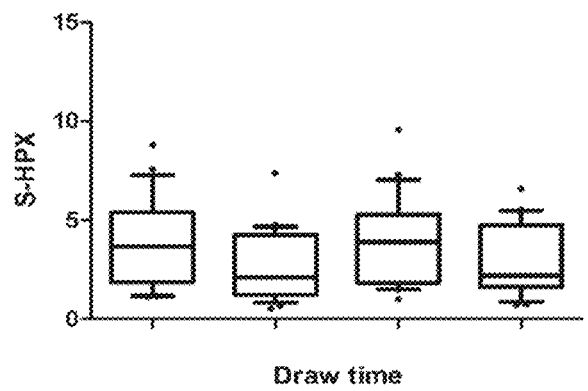
FIG. 3B is a graph depicting direct quantification of the ratio (S-HPX) of di-sialylated to mono-sialylated glycoforms of the peptide TPLPPTSAHGNVAE-GETKPDPVTER (SEQ ID NO:1) of HPX for 23 healthy volunteers at 4 different blood draw times. The box and whisker plots represents median, $25^{th}$-$75^{th}$ percentile, range of values, and outliers. *, significantly different at p<0.01 from control.

Quantification of S-HPX in the Discovery set showed a significant increase in the fibrotic HALT-C participants compared to disease-free controls and further increase in the cirrhotic patients (Mann-Whitney U test, p<0.001) (FIG. 3A). At the same time, analysis of S-HPX in disease-free controls (n=23) that provided samples at four different times in the span of a year showed consistently low S-HPX without significant differences between the draw times (FIG. 3B). Summary statistics of the S-HPX quantification in both the Discovery and the Verification sets of samples are provided in Table 6. No significant influence of age, gender or race on S-HPX was observed in any of the groups. To evaluate influence of IFN treatment on S-HPX, a similar proportion of participants in the IFN treatment and control arms of the HALT-C trial was selected in the Discovery set. Analysis showed a trend to lower S-HPX in the IFN treatment arm in both the fibrotic and cirrhotic groups but the changes did not reach statistical significance (Table 3). Since the low-dose interferon treatment is not clinically used, only patients from the control arm of the HALT-C trial were included in the Validation set.

TABLE 6

S-HPX measurement in the Discovery and Validation sets of participants

| | N | Mean ± SD | Median (Range) | p-value |
|---|---|---|---|---|
| Discovery | | | | |
| CTRL | 23 | 14.7 ± 6.67 | 13.3 (4.81, 32.0) | <0.001 |
| FIB | 22 | 24.9 ± 14.2 | 21.0 (11.0, 76.0) | |
| CIR | 24 | 68.6 ± 38.5 | 65.3 (19.5, 156.1) | |
| Validation | | | | |
| CTRL | 15 | 16.2 ± 7.36 | 15.0 (7.91, 32.8) | <0.001 |
| FIB | 15 | 25.8 ± 11.1 | 23.5 (15.2, 60.0) | |
| CIR | 15 | 54.9 ± 38.9 | 46.4 (13.1, 177.6) | |

Correlation analyses of clinical and demographic variables with S-HPX in the Discovery set showed multiple significant associations of weak to moderate strength (Table 7).

TABLE 7

Associations between clinical variables and S-HPX. Spearman correlation coefficients were evaluated in all samples combined and in the fibrosis and cirrhosis groups, separately.

| | All (n = 46) | | Fibrosis (n = 22) | | Cirrhosis (n = 24) | |
|---|---|---|---|---|---|---|
| | $r_s$ | p-value | $r_s$ | p-value | $r_s$ | p-value |
| Age | −0.034 | 0.832 | 0.160 | 0.489 | 0.017 | 0.945 |
| Bilirubin [mg/dL] | 0.409 | 0.008* | 0.088 | 0.705 | 0.393 | 0.086 |
| Creatinine [mg/dL] | −0.166 | 0.270 | 0.129 | 0.568 | −0.363 | 0.081 |
| INR | 0.390 | 0.012* | 0.039 | 0.866 | 0.006 | 0.979 |
| MELD | 0.279 | 0.061 | 0.215 | 0.338 | 0.134 | 0.534 |
| AFP [ng/mL] | 0.578 | <0.001* | 0.429 | 0.052 | 0.439 | 0.053 |
| Albumin [g/dL] | −0.436 | 0.004* | −0.040 | 0.862 | −0.511 | 0.021* |
| Alk. phosphastase [U/L] | 0.195 | 0.193 | 0.116 | 0.608 | 0.185 | 0.387 |
| ALT (U/L) | 0.337 | 0.031* | −0.163 | 0.480 | 0.346 | 0.135 |
| AST (U/L) | 0.520 | 0.001* | −0.087 | 0.709 | 0.747 | 0.001* |
| Platelet ($10^9$/L) | −0.564 | <0.001* | −0.462 | 0.035* | −0.358 | 0.121 |
| FIB-4 | 0.612 | <0.001* | 0.366 | 0.103 | 0.574 | 0.008* |
| APRI | 0.562 | <0.001* | 0.158 | 0.493 | 0.589 | 0.006* |

*Significance level <0.05.

Figure 7:
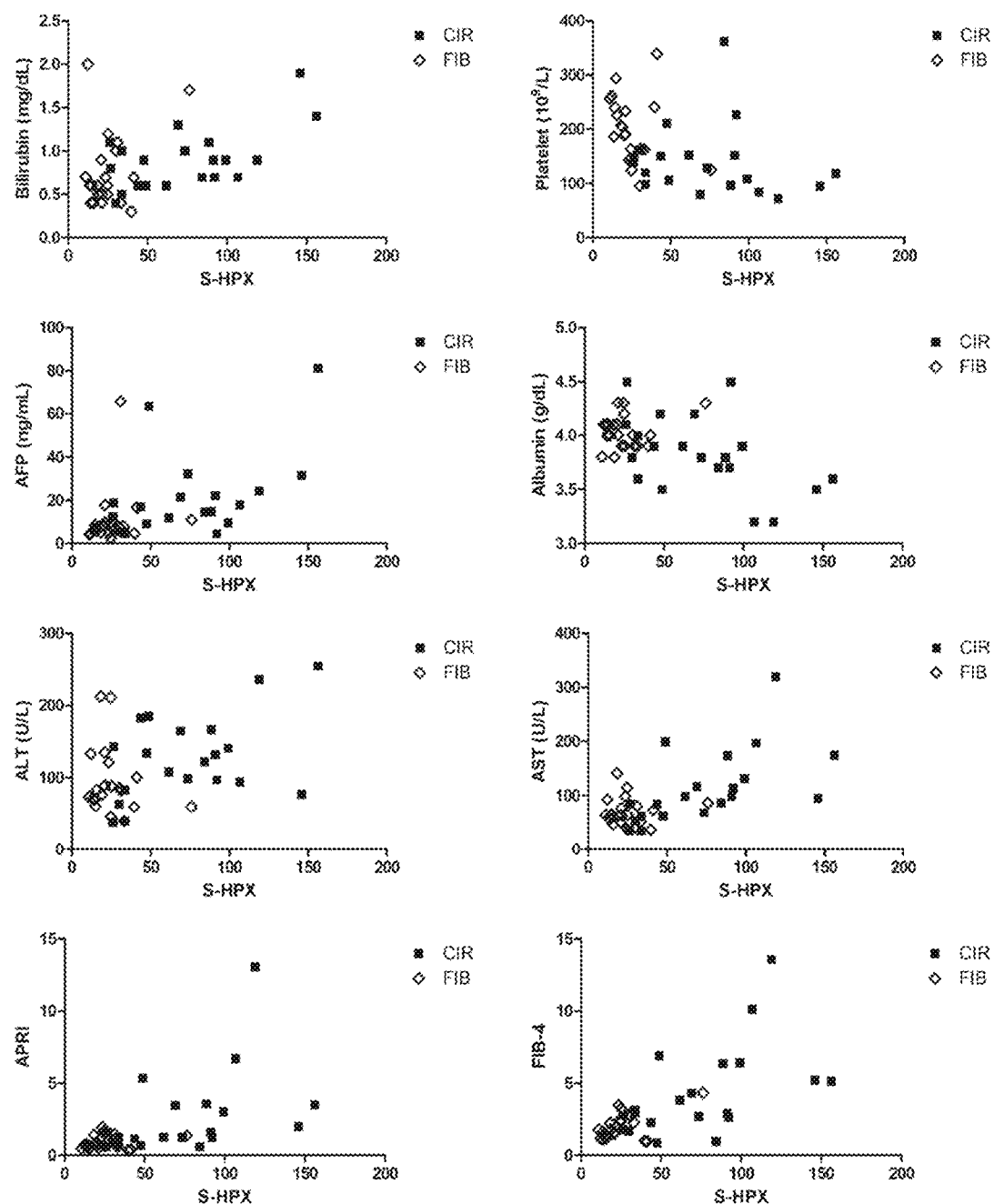
FIG. 7 is a series of eight graphs depicting significant associations of S-HPX and indicated other clinical variables (bilirubin, platelets, AFP, albumin, ALT, AST, APRI, FIB-4) in groups of fibrotic (FIB, open symbols, n=22) and cirrhotic (CIR, filled symbols, n=24) participants.

S-HPX was correlated with AFP ($r_s$=0.53; p<0.001), bilirubin ($r_s$=0.41; p=0.008), INR ($r_s$=0.39; p=0.012), ALT ($r_s$=0.34; p=0.031), and AST ($r_s$=0.52; p=0.001), while inversely correlated with platelet count ($r_s$=−0.56; p<0.001) and albumin ($r_s$=−0.44; p=0.004). This means that S-HPX is also positively correlated with the FIB-4 ($r_s$=−0.60; p<0.001) and APRI ($r_s$=0.53; p<0.001) indexes based on combinations of the above variables. These associations were significant to a greater degree in the cirrhotic patients (Table 7). Scatter plots of the variables significantly associated with S-HPX document further these relationships (FIG. 7).

A simple logistic model using S-HPX as an independent variable was used to determine the cutoff values of S-HPX for separation of the healthy, fibrotic, and cirrhotic participants in the Discovery set. The resulting model performs well with AuROCs of 0.77 and 0.90 in separating patients who developed fibrosis from the controls, and cirrhotic patients from the controls, respectively (FIG. 4A). When the S-HPX cutoff between the fibrotic and control groups was set at 13.5, sensitivity is 91% and specificity is 52%. With the cutoff point 42.5 between cirrhotic and fibrotic patient, sensitivity is 96% and specificity is 71%.

The diagnostic performance of S-HPX was further tested using 45 Verification samples using the LC-MS/MS-MRM measurement of S-HPX and cutoffs determined in the Discovery set. The results show an AuROC of 0.82 (FIG. 4B) for the separation of fibrotic and disease-free groups, which is better than the AuROC of 0.77 in the Discovery set. Here it was not possible to compare S-HPX to other measures of fibrosis due to lack of other variables in controls. However, diagnostic performance of platelet count, AFP, and the FIB-4 and APRI indexes were compared with S-HPX in distinguishing the cirrhotic patients from the fibrotic patients. S-HPX achieved AuROC of 0.84 which is higher than any other measures with sensitivity and specificity of S-HPX being 60% and 93%, respectively (Table 4).

In conclusion, for the first time, it has been shown that di-sialylated O-glycoform of HPX is elevated in liver disease, and an LC-MS/MS-MRM assay has been established for its quantification in serum. The ratio of di-sialylated O-glycoform to mono-sialylated O-glycoform of HPX, S-HPX, could serve as a simple indicator of liver fibrosis, alone or in combination with other factors currently used to classify liver disease. Analysis of the sialylated glycoform at a specific site of HPX attachment directly in unfractionated serum facilitates clinical applicability of the robust MRM quantification method.

We claim:

1. An in vitro method of assessing liver fibrosis in a subject, comprising quantitatively measuring di-sialylated and mono-sialylated O-glycoforms of a peptide fragment of hemopexin in a test serum sample obtained from a test subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from a reference subject, wherein the reference subject is free of liver fibrosis; and identifying the test subject as having liver fibrosis when the measured amount of di-sialylated O-glycoform of the peptide fragment of hemopexin in the test serum sample is increased, and the measured amount of mono-sialylated O-glycoform of the peptide fragment of hemopexin in the test serum sample is decreased, as compared to corresponding measured amounts in the reference serum sample.

2. The method of claim 1, wherein the amino acid sequence of the peptide fragment of hemopexin consists of SEQ ID NO:1.

3. The method of claim 1, wherein the measuring comprises LC-MS/MS-MRM (liquid chromatography/tandem mass spectrometry/multiple reaction monitoring).

4. The method of claim 1, wherein the measuring comprises LC/MS3 (liquid chromatography with triple-stage mass spectrometric detection).

5. An in vitro method of assessing liver fibrosis in a subject, comprising quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;

comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the subject, wherein the reference serum sample was obtained from the subject earlier in time than the test serum sample; and identifying the subject as having increased liver fibrosis when the measured amount of di-sialylated O-glycoform of the peptide fragment of hemopexin in the test serum sample is increased, and the measured amount of mono-sialylated O-glycoform of the peptide fragment of hemopexin in the test serum sample is decreased, as compared to corresponding measured amounts in the reference serum sample, or identifying the subject as having decreased liver fibrosis when the measured amount of di-sialylated O-glycoform of the peptide fragment of hemopexin in the test serum sample is decreased, and the measured amount of mono-sialylated O-glycoform of the peptide fragment of hemopexin in the test serum sample is increased, as compared to corresponding measured amounts in the reference serum sample.

6. The method of claim 5, wherein the amino acid sequence of the peptide fragment of hemopexin consists of SEQ ID NO:1.

7. A method of assessing efficacy of an agent for the treatment of liver fibrosis, wherein the agent is selected from the group consisting of anti-fibrosis agents and candidate anti-fibrosis agents, comprising
quantitatively measuring di-sialylated and mono-sialylated O-glycoforms of a peptide fragment of hemopexin in a first test serum sample obtained from a subject, wherein the amino acid sequence of the peptide fragment of hemopexin comprises SEQ ID NO:1;
administering the agent to the subject;
quantitatively measuring di-sialylated and mono-sialylated O-glycoforms of the peptide fragment of hemopexin in a second test serum sample obtained from the subject;
comparing the measured amounts of di-sialylated and mono-sialylated O-glycoforms of the peptide fragment of hemopexin in the first test serum sample to the measured amounts of di-sialylated and mono-sialylated O-glycoforms of the peptide fragment of hemopexin in the second serum sample, wherein the second test serum sample was obtained after the administering and later in time than the first test serum sample; and
identifying the agent as effective for treating liver fibrosis when the measured amount of di-sialylated O-glycoform of the peptide fragment of hemopexin in the second test serum sample is decreased, and the measured amount of mono-sialylated O-glycoform of the peptide fragment of hemopexin in the second test serum sample is increased, as compared to corresponding measured amounts in the first test serum sample.

8. The method of claim 7, wherein the amino acid sequence of the peptide fragment of hemopexin consists of SEQ ID NO:1.

9. The method of claim 7, further comprising identifying the agent as ineffective for treating liver fibrosis when the measured amount of di-sialylated O-glycoform of the peptide fragment of hemopexin in the second test serum sample is increased, and the measured amount of mono-sialylated O-glycoform of the peptide fragment of hemopexin in the second test serum sample is decreased, as compared to corresponding measured amounts in the first test serum sample.

10. The method of claim 7, wherein the agent is an anti-fibrosis agent.

11. The method of claim 7, wherein the agent is a candidate anti-fibrosis agent.

12. The method of claim 7, wherein the agent is selected from the group consisting of interferon alfa-2b, PEG-interferon alfa-2b, PEG-interferon alfa-2a, lamivudine, adefovir, telbivudine, entecavir, ribavirin, boceprivir, telaprevir, simeprevir, sofosbuvir, ledipasvir/sofosbuvir, sofosbuvir/velpatasvir, ombitasvir/paritaprevir/ritonavir, daclatasvir, dasabuvir, CB1 antagonist, 5HT-2B receptor antagonist, angiotensin-converting enzyme (ACE) inhibitor, angiotensin II type 1 (AT1) receptor blocker, endothelin 1 (ET-1) receptor antagonist, adiponectin, ghrelin, PDGF receptor antagonist, imatinib, nilotinib, tissue inhibitors of metalloproteinases (TIMPs), sulfasalazine, gliotoxin, nonsteroidal anti-inflammatory drugs (NSAIDs), and any combination thereof.

13. A method of treating liver fibrosis, comprising
quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;
comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the subject, wherein the reference serum sample was obtained earlier in time than the test serum sample;
identifying the subject as having increased liver fibrosis when the measured amount of di-sialylated O-glycoform of the peptide fragment of hemopexin in the test serum sample is increased, and the measured amount of mono-sialylated O-glycoform of the peptide fragment of hemopexin in the test serum sample is decreased, as compared to corresponding measured amounts in the reference serum sample; and
administering to the subject having increased liver fibrosis an initial amount or an increased amount of an anti-fibrosis agent.

14. The method of claim 13, wherein the amino acid sequence of the peptide fragment of hemopexin consists of SEQ ID NO: 1.

15. The method of claim 13, wherein the subject having increased liver fibrosis is administered an initial amount of the anti-fibrosis agent.

16. The method of claim 13, wherein the subject having increased liver fibrosis is administered an increased amount of the anti-fibrosis agent.

17. The method of claim 13, wherein the anti-fibrosis agent is selected from the group consisting of interferon alfa-2b, PEG-interferon alfa-2b, PEG-interferon alfa-2a, lamivudine, adefovir, telbivudine, entecavir, ribavirin, boceprivir, telaprevir, simeprevir, sofosbuvir, ledipasvir/sofosbuvir, sofosbuvir/velpatasvir, ombitasvir/paritaprevir/ritonavir, daclatasvir, dasabuvir, CB1 antagonist, 5HT-2B receptor antagonist, angiotensin-converting enzyme (ACE) inhibitor, angiotensin II type 1 (AT1) receptor blocker, endothelin 1 (ET-1) receptor antagonist, adiponectin, ghrelin, PDGF receptor antagonist, imatinib, nilotinib, tissue inhibitors of metalloproteinases (TIMPs), sulfasalazine, gliotoxin, nonsteroidal anti-inflammatory drugs (NSAIDs), and any combination thereof.

18. A method of treating liver fibrosis, comprising
quantitatively measuring di-sialylated and mono-sialylated O-glycoforms of a peptide fragment of hemopexin in a test serum sample obtained from a subject, wherein the amino acid sequence of the peptide fragment of hemopexin comprises SEQ ID NO:1;
comparing the measured amounts of di-sialylated and mono-sialylated O-glycoforms of the peptide fragment of hemopexin in the test serum sample to measured amounts of di-sialylated and mono-sialylated O-glycoforms of the peptide fragment of hemopexin in a reference serum sample obtained from the test subject, wherein the reference serum sample was obtained earlier in time than the test serum sample;
identifying the test subject as having decreased liver fibrosis when the measured amount of di-sialylated O-glycoform of the peptide fragment of hemopexin in the test serum sample is decreased, and the measured amount of mono-sialylated O-glycoform of the peptide fragment of hemopexin in the test serum sample is increased, as compared to corresponding measured amounts in the reference serum sample; and administering to the subject having decreased liver fibrosis a continued amount or a decreased amount of an anti-fibrosis agent.

19. The method of claim 18, wherein the amino acid sequence of the peptide fragment of hemopexin consists of SEQ ID NO:1.

20. The method of claim 18, wherein the anti-fibrosis agent is selected from the group consisting of interferon alfa-2b, PEG-interferon alfa-2b, PEG-interferon alfa-2a, lamivudine, adefovir, telbivudine, entecavir, ribavirin, boceprivir, telaprevir, simeprevir, sofosbuvir, ledipasvir/sofosbuvir, sofosbuvir/velpatasvir, ombitasvir/paritaprevir/ritonavir, daclatasvir, dasabuvir, CB1 antagonist, 5HT-2B receptor antagonist, angiotensin-converting enzyme (ACE) inhibitor, angiotensin II type 1 (AT1) receptor blocker, endothelin 1 (ET-1) receptor antagonist, adiponectin, ghrelin, PDGF receptor antagonist, imatinib, nilotinib, tissue inhibitors of metalloproteinases (TIMPs), sulfasalazine, gliotoxin, non-steroidal anti-inflammatory drugs (NSAIDs), and any combination thereof.

* * * * *

UNITED STATES PATENT AND TRADEMARK OFFICE
CERTIFICATE OF CORRECTION

| | |
|---|---|
| PATENT NO. | : 11,035,865 B2 |
| APPLICATION NO. | : 16/329926 |
| DATED | : June 15, 2021 |
| INVENTOR(S) | : Goldman et al. |

It is certified that error appears in the above-identified patent and that said Letters Patent is hereby corrected as shown below:

In the Specification

At Column 1, Line 12 delete:
"STATEMENT REGARDING FEDERALLY SPONSORED RESEARCH OR DEVELOPMENT
This invention was made with government support under grant numbers U01 CA168926 and R01 CA135069 awarded by the National Institutes of Health, and grant number P30 CA51008 awarded by the National Cancer Institute. The Government has certain rights in the invention."

And insert:
--STATEMENT REGARDING FEDERALLY SPONSORED RESEARCH OR DEVELOPMENT
This invention was made with government support under grant numbers CA051008, CA135069, and CA168926 awarded by the National Institutes of Health. The Government has certain rights in the invention.--

Signed and Sealed this
Twenty-third Day of January, 2024

*Katherine Kelly Vidal*

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial sequence
<220> FEATURE:
<223> OTHER INFORMATION: Synthetic peptide

<400> SEQUENCE: 1

Thr Pro Leu Pro Pro Thr Ser Ala His Gly Asn Val Ala Glu Gly Glu
1               5                   10                  15

Thr Lys Pro Asp Pro Val Thr Glu Arg
            20                  25
```